(12) United States Patent
Torrie et al.

(10) Patent No.: US 9,492,160 B2
(45) Date of Patent: Nov. 15, 2016

(54) CLOSURE DEVICE AND METHOD FOR TISSUE REPAIR

(71) Applicant: Smith & Nephew, Inc., Memphis, TN (US)

(72) Inventors: Paul A. Torrie, Marblehead, MA (US); George Sikora, Bridgewater, MA (US); Raymond A. Bojarski, Attleboro, MA (US); Steven W. Ek, Bolton, MA (US)

(73) Assignee: Smith & Nephew, Inc., Memphis, TN (US)

(*) Notice: Subject to any disclaimer, the term of this patent is extended or adjusted under 35 U.S.C. 154(b) by 91 days.

(21) Appl. No.: 14/454,243

(22) Filed: Aug. 7, 2014

(65) Prior Publication Data

US 2014/0350599 A1    Nov. 27, 2014

Related U.S. Application Data

(63) Continuation of application No. 13/944,682, filed on Jul. 17, 2013, now Pat. No. 8,834,524, which is a continuation of application No. 11/025,837, filed on Dec. 30, 2004, now Pat. No. 8,512,375, which is a continuation of application No. 09/704,926, filed on Nov. 2, 2000, now Pat. No. 7,153,312, which is a continuation of application No. 09/453,120, filed on Dec. 2, 1999, now abandoned.

(Continued)

(51) Int. Cl.
*A61B 17/04* (2006.01)
*A61B 17/06* (2006.01)
*A61F 2/08* (2006.01)

(52) U.S. Cl.
CPC ....... *A61B 17/0401* (2013.01); *A61B 17/0469* (2013.01); *A61B 17/06166* (2013.01);

(Continued)

(58) Field of Classification Search
CPC .............. A61B 2017/0401; A61B 2017/0446; A61B 2017/0456; A61B 2017/0458; A61B 2017/0459; A61B 2017/0462; A61B 2017/0464

See application file for complete search history.

(56) References Cited

U.S. PATENT DOCUMENTS

| 233,475 A | 10/1880 | Cook et al. |
| 261,501 A | 7/1882 | Vandermark |

(Continued)

FOREIGN PATENT DOCUMENTS

| EP | 0108912 | 5/1984 |
| EP | 0260970 | 3/1988 |

(Continued)

OTHER PUBLICATIONS

Notification of Reason for Rejection for Japanese Application No. 2011-039140, mailed Sep. 26, 2012.

(Continued)

*Primary Examiner* — Tuan V Nguyen
(74) *Attorney, Agent, or Firm* — Burns & Levinson LLP; Joseph M. Maraia

(57) ABSTRACT

A method of closing a tissue wound includes providing a wound closure device having a first anchor, a second anchor, and a flexible member movably attached to the second anchor, positioning the first anchor against tissue, passing the flexible member across the wound, positioning the second anchor against tissue, and pulling on a free end of the flexible member to shorten a length of the flexible member between the first and second anchors, thereby closing the wound. A wound closure device includes a first anchor, a second anchor; and a flexible member connecting the first anchor to the second anchor, the flexible member being movably attached to the second anchor, such that pulling on a free end of the flexible member shortens a length of the flexible member between the first and second anchors.

16 Claims, 46 Drawing Sheets

(52) U.S. Cl.
CPC  *A61B2017/0409* (2013.01); *A61B 2017/0414* (2013.01); *A61B 2017/0417* (2013.01); *A61B 2017/0459* (2013.01); *A61B 2017/0464* (2013.01); *A61B 2017/0475* (2013.01); *A61B 2017/0477* (2013.01); *A61B 2017/0496* (2013.01); *A61F 2/0811* (2013.01); *Y10T 24/3916* (2015.01)

(56) References Cited

U.S. PATENT DOCUMENTS

| | | |
|---|---|---|
| 1,635,066 A | 7/1927 | Wells |
| 2,479,464 A | 8/1949 | Bliss |
| 2,610,631 A | 9/1952 | Calicchio |
| 2,880,728 A | 4/1959 | Rights |
| 2,881,762 A | 4/1959 | Lowrie |
| 3,409,014 A | 11/1968 | Grant |
| 3,470,875 A | 10/1969 | Johnson |
| 3,618,447 A | 11/1971 | Goins |
| 3,664,345 A | 5/1972 | Dabbs et al. |
| 3,716,058 A | 2/1973 | Tanner, Jr. |
| 3,752,516 A | 8/1973 | Mumma |
| 3,757,629 A | 9/1973 | Schnieider |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,867,944 A | 2/1975 | Samuels |
| 3,871,379 A | 3/1975 | Clarke |
| 3,910,281 A | 10/1975 | Kletschka et al. |
| 3,946,740 A | 3/1976 | Bassett |
| 3,976,079 A | 8/1976 | Samuels et al. |
| 3,977,050 A | 8/1976 | Perez |
| 3,985,138 A | 10/1976 | Jarvik |
| 4,006,747 A | 2/1977 | Kronenthal et al. |
| 4,039,753 A | 8/1977 | Balogh et al. |
| 4,105,349 A | 8/1978 | Kupperman et al. |
| 4,141,087 A | 2/1979 | Shalaby et al. |
| 4,144,876 A | 3/1979 | DeLeo |
| 4,160,453 A | 7/1979 | Miller |
| 4,186,514 A | 2/1980 | Oquita |
| 4,235,238 A | 11/1980 | Ogiu et al. |
| 4,316,469 A | 2/1982 | Kapitanov |
| 4,326,531 A | 4/1982 | Shimonaka |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,570,623 A | 2/1986 | Ellison et al. |
| 4,595,007 A | 6/1986 | Mericle |
| 4,596,249 A | 6/1986 | Freda et al. |
| 4,602,635 A | 7/1986 | Mulhollan et al. |
| 4,616,650 A | 10/1986 | Green et al. |
| 4,624,254 A | 11/1986 | McGarry et al. |
| 4,635,637 A | 1/1987 | Schreiber |
| 4,636,121 A | 1/1987 | Miller |
| 4,641,652 A | 2/1987 | Hutterer et al. |
| 4,662,068 A | 5/1987 | Polonsky |
| 4,705,040 A | 11/1987 | Miller et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,741,330 A | 5/1988 | Hayhurst |
| 4,741,336 A | 5/1988 | Failla et al. |
| 4,750,492 A | 6/1988 | Jacobs |
| 4,760,848 A | 8/1988 | Hasson |
| 4,781,190 A | 11/1988 | Lee |
| 4,809,695 A | 3/1989 | Gwathmey et al. |
| 4,823,794 A | 4/1989 | Pierce |
| 4,841,960 A | 6/1989 | Garner |
| 4,846,793 A | 7/1989 | Leonard et al. |
| 4,858,608 A | 8/1989 | McQuilkem |
| 4,873,976 A | 10/1989 | Schreiber |
| 4,884,572 A | 12/1989 | Bays et al. |
| 4,887,601 A | 12/1989 | Richards |
| 4,890,615 A | 1/1990 | Caspari et al. |
| 4,895,148 A | 1/1990 | Bays et al. |
| 4,899,743 A | 2/1990 | Nicholson et al. |
| 4,917,699 A | 4/1990 | Chervitz |
| 4,923,461 A | 5/1990 | Caspari et al. |
| 4,950,285 A | 8/1990 | Wilk |
| 4,961,741 A | 10/1990 | Hayhurst |
| 4,983,176 A | 1/1991 | Cushman et al. |
| 4,994,028 A | 2/1991 | Leonard et al. |
| 5,037,422 A | 8/1991 | Hayhurst |
| 5,041,129 A | 8/1991 | Hayhurst et al. |
| 5,046,513 A | 9/1991 | Gatturna et al. |
| 5,053,047 A | 10/1991 | Yoon |
| 5,059,201 A | 10/1991 | Asnis |
| 5,078,731 A | 1/1992 | Hayhurst |
| 5,084,050 A | 1/1992 | Draenert |
| 5,084,058 A | 1/1992 | Li |
| 5,087,263 A | 2/1992 | Li |
| 5,100,415 A | 3/1992 | Hayhurst |
| 5,102,421 A | 4/1992 | Anspach, Jr. |
| 5,123,913 A | 6/1992 | Wilk et al. |
| 5,141,520 A | 8/1992 | Goble et al. |
| 5,149,329 A | 9/1992 | Richardson |
| 5,154,189 A | 10/1992 | Oberlander |
| D331,626 S | 12/1992 | Hayhurst |
| 5,178,629 A | 1/1993 | Kammerer |
| 5,203,787 A | 4/1993 | Noblitt et al. |
| 5,207,753 A | 5/1993 | Badrinath |
| 5,211,650 A | 5/1993 | Noda |
| 5,217,470 A | 6/1993 | Weston |
| 5,219,359 A | 6/1993 | McQuilken et al. |
| 5,224,946 A | 7/1993 | Hayhurst et al. |
| 5,234,426 A | 8/1993 | Rank et al. |
| 5,236,445 A | 8/1993 | Hayhurst et al. |
| 5,246,441 A | 9/1993 | Ross et al. |
| 5,258,015 A | 11/1993 | Li et al. |
| 5,258,016 A | 11/1993 | DiPoto et al. |
| 5,261,914 A | 11/1993 | Warren |
| 5,268,001 A | 12/1993 | Nicholson et al. |
| 5,269,809 A | 12/1993 | Hayhurst et al. |
| 5,279,539 A | 1/1994 | Bohan et al. |
| 5,282,809 A | 2/1994 | Kammerer et al. |
| 5,318,577 A | 6/1994 | Li |
| 5,320,633 A | 6/1994 | Allen et al. |
| 5,336,229 A | 8/1994 | Noda |
| 5,336,231 A | 8/1994 | Adair |
| 5,342,369 A | 8/1994 | Harryman, II |
| 5,354,299 A | 10/1994 | Coleman |
| 5,364,408 A | 11/1994 | Gordon |
| 5,417,691 A | 5/1995 | Hayhurst |
| 5,417,692 A | 5/1995 | Goble et al. |
| 5,437,680 A | 8/1995 | Yoon |
| 5,439,684 A | 8/1995 | Prewett et al. |
| 5,441,502 A | 8/1995 | Bartlett |
| 5,447,512 A | 9/1995 | Wilson et al. |
| 5,458,081 A | 10/1995 | Reichert |
| 5,458,608 A | 10/1995 | Wortrich |
| 5,467,786 A | 11/1995 | Allen et al. |
| 5,474,572 A | 12/1995 | Hayhurst |
| 5,490,750 A | 2/1996 | Gundy |
| 5,496,331 A | 3/1996 | Xu et al. |
| 5,500,000 A | 3/1996 | Feagin et al. |
| 5,520,696 A | 5/1996 | Wenstrom, Jr. |
| 5,520,700 A | 5/1996 | Beyar et al. |
| 5,520,921 A | 5/1996 | Chalifoux |
| 5,522,820 A | 6/1996 | Caspari et al. |
| 5,522,844 A | 6/1996 | Johnson |
| 5,527,342 A | 6/1996 | Pietzak et al. |
| 5,545,178 A | 8/1996 | Kensey et al. |
| 5,554,171 A | 9/1996 | Gatturna |
| 5,562,684 A | 10/1996 | Kammerer |
| 5,573,286 A | 11/1996 | Rogozinski |
| 5,593,424 A | 1/1997 | Northrup, III |
| 5,601,557 A | 2/1997 | Hayhurst |
| 5,601,558 A | 2/1997 | Torrie et al. |
| 5,607,432 A | 3/1997 | Fucci |
| 5,609,597 A | 3/1997 | Lehrer |
| 5,641,256 A | 6/1997 | Gundy |
| 5,643,319 A | 7/1997 | Green et al. |
| 5,643,321 A | 7/1997 | McDevitt |

(56) References Cited

U.S. PATENT DOCUMENTS

| | | |
|---|---|---|
| 5,647,874 A | 7/1997 | Hayhurst |
| 5,658,299 A | 8/1997 | Hart |
| 5,665,112 A | 9/1997 | Thal |
| 5,690,676 A | 11/1997 | DiPotto et al. |
| 5,690,678 A | 11/1997 | Johnson |
| 5,702,422 A | 12/1997 | Stone |
| 5,702,462 A | 12/1997 | Oberlander |
| 5,713,904 A | 2/1998 | Errico et al. |
| 5,716,359 A | 2/1998 | Ojima et al. |
| 5,720,753 A | 2/1998 | Sander |
| 5,720,765 A | 2/1998 | Thal |
| 5,725,529 A | 3/1998 | Nicholson et al. |
| 5,725,556 A | 3/1998 | Moser et al. |
| 5,725,581 A | 3/1998 | Branemark |
| 5,728,109 A | 3/1998 | Schulze et al. |
| 5,728,136 A | 3/1998 | Thal |
| 5,730,744 A | 3/1998 | Justin et al. |
| 5,746,754 A | 5/1998 | Chan |
| 5,749,898 A | 5/1998 | Schulze et al. |
| 5,782,862 A | 7/1998 | Bonuti |
| 5,782,864 A | 7/1998 | Lizardi |
| 5,797,928 A | 8/1998 | Kogasaka |
| 5,810,769 A | 9/1998 | Schlegel et al. |
| 5,810,848 A | 9/1998 | Hayhurst |
| 5,814,069 A | 9/1998 | Schulze et al. |
| RE36,020 E | 12/1998 | Moore et al. |
| 5,843,084 A | 12/1998 | Hart et al. |
| 5,843,087 A | 12/1998 | Jensen et al. |
| 5,846,254 A | 12/1998 | Schulze et al. |
| 5,860,983 A | 1/1999 | Wenstrom, Jr. |
| 5,871,490 A | 2/1999 | Schulze et al. |
| 5,891,168 A | 4/1999 | Thal |
| 5,893,592 A | 4/1999 | Schulze et al. |
| 5,893,856 A | 4/1999 | Jacob et al. |
| 5,893,880 A | 4/1999 | Egan et al. |
| 5,895,395 A | 4/1999 | Yeung |
| 5,897,564 A | 4/1999 | Schulze et al. |
| 5,902,321 A | 5/1999 | Caspari et al. |
| 5,921,986 A | 7/1999 | Bonutti |
| 5,928,244 A | 7/1999 | Tovey et al. |
| 5,941,439 A | 8/1999 | Kammerer et al. |
| 5,948,002 A | 9/1999 | Bonutti |
| 5,954,747 A | 9/1999 | Clark |
| 5,964,765 A | 10/1999 | Fenton |
| 5,964,783 A | 10/1999 | Grafton et al. |
| 5,976,127 A | 11/1999 | Lax |
| 5,980,524 A | 11/1999 | Justin et al. |
| 5,989,252 A | 11/1999 | Fumex |
| 5,993,458 A | 11/1999 | Vaitekunas et al. |
| 6,024,758 A | 2/2000 | Thal |
| 6,027,523 A | 2/2000 | Schieding |
| 6,039,753 A | 3/2000 | Meislin |
| 6,045,574 A | 4/2000 | Thal |
| 6,056,320 A | 5/2000 | Khalifa et al. |
| 6,063,106 A | 5/2000 | Gibson |
| 6,066,146 A | 5/2000 | Carroll et al. |
| 6,074,395 A | 6/2000 | Trott et al. |
| 6,096,038 A | 8/2000 | Michelson |
| 6,096,060 A | 8/2000 | Fitts et al. |
| 6,117,160 A | 9/2000 | Bonutti |
| RE36,974 E | 11/2000 | Bonutti |
| 6,143,017 A | 11/2000 | Thal |
| 6,146,387 A | 11/2000 | Trott et al. |
| 6,152,934 A | 11/2000 | Harper et al. |
| 6,152,936 A | 11/2000 | Christy et al. |
| 6,156,039 A | 12/2000 | Thal |
| 6,165,203 A | 12/2000 | Krebs |
| 6,174,324 B1 | 1/2001 | Egan et al. |
| 6,193,754 B1 | 2/2001 | Seedhom |
| 6,217,591 B1 | 4/2001 | Egan et al. |
| 6,283,996 B1 | 9/2001 | Chervitz et al. |
| 6,286,746 B1 | 9/2001 | Egan et al. |
| 6,306,158 B1 | 10/2001 | Bartlett |
| 6,306,159 B1 | 10/2001 | Schwartz et al. |
| 6,319,263 B1 | 11/2001 | Levinson |
| 6,319,271 B1* | 11/2001 | Schwartz ............ A61B 17/0401 289/2 |
| 6,358,271 B1 | 3/2002 | Egan et al. |
| 6,409,743 B1 | 6/2002 | Fenton, Jr. |
| 6,432,123 B2 | 8/2002 | Schwartz et al. |
| 6,491,707 B2 | 12/2002 | Makower et al. |
| 6,500,184 B1 | 12/2002 | Chan et al. |
| 6,520,980 B1 | 2/2003 | Foester |
| 6,524,317 B1 | 2/2003 | Richart et al. |
| 6,527,795 B1 | 3/2003 | Lizardi |
| 6,533,802 B2 | 3/2003 | Bojarski et al. |
| 6,554,852 B1 | 4/2003 | Oberlander |
| 6,585,730 B1 | 7/2003 | Foerster |
| 6,635,073 B2 | 10/2003 | Bonutti |
| 6,641,596 B1 | 11/2003 | Lizardi |
| 6,652,563 B2 | 11/2003 | Dreyfuss |
| 6,656,182 B1 | 12/2003 | Hayhurst |
| 6,669,705 B2 | 12/2003 | Westhaver et al. |
| 6,692,499 B2 | 2/2004 | Tormala et al. |
| 6,692,516 B2 | 2/2004 | West, Jr. et al. |
| 6,736,829 B1 | 5/2004 | Li et al. |
| 6,770,076 B2 | 8/2004 | Foerster |
| 6,855,157 B2 | 2/2005 | Foerster et al. |
| 6,923,824 B2 | 8/2005 | Morgan et al. |
| 6,972,019 B2 | 12/2005 | Michelson |
| 6,972,027 B2 | 12/2005 | Fallin et al. |
| 7,041,120 B2 | 5/2006 | Li et al. |
| 7,153,312 B1 | 12/2006 | Torrie et al. |
| 7,163,563 B2 | 1/2007 | Schwartz et al. |
| 7,500,983 B1 | 3/2009 | Kaiser et al. |
| 8,834,524 B2* | 9/2014 | Torrie ................. A61B 17/0401 24/129 R |
| 2001/0010005 A1 | 7/2001 | Kammerer et al. |
| 2002/0019649 A1 | 2/2002 | Sikora et al. |
| 2002/0052629 A1 | 5/2002 | Morgan et al. |
| 2002/0091959 A1 | 7/2002 | Klien et al. |
| 2002/0095181 A1 | 7/2002 | Beyar |
| 2002/0133159 A1 | 9/2002 | Jackson |
| 2002/0147463 A1 | 10/2002 | Martinek |
| 2002/0156500 A1 | 10/2002 | Storz-Irion et al. |
| 2002/0165548 A1 | 11/2002 | Jutley |
| 2002/0173821 A1 | 11/2002 | Fenton et al. |
| 2003/0070004 A1 | 4/2003 | Mukundan et al. |
| 2003/0109900 A1 | 6/2003 | Martinek |
| 2003/0120277 A1 | 6/2003 | Berger |
| 2003/0130694 A1 | 7/2003 | Borjaski et al. |
| 2003/0236555 A1 | 12/2003 | Thornes |
| 2004/0002734 A1 | 1/2004 | Fallin et al. |
| 2004/0037094 A1 | 2/2004 | Muegge et al. |
| 2004/0092937 A1 | 5/2004 | Criscuolo et al. |
| 2004/0133238 A1 | 7/2004 | Cerier |
| 2004/0133239 A1 | 7/2004 | Singhatat |
| 2004/0138683 A1 | 7/2004 | Shelton et al. |
| 2004/0243131 A1 | 12/2004 | Dirks et al. |
| 2004/0267317 A1 | 12/2004 | Higgins et al. |
| 2005/0033363 A1 | 2/2005 | Bojarski et al. |
| 2005/0037150 A1 | 2/2005 | Lijima et al. |
| 2005/0187577 A1 | 8/2005 | Selvitelli et al. |
| 2005/0277961 A1 | 12/2005 | Stone et al. |
| 2005/0277986 A1 | 12/2005 | Foester et al. |
| 2006/0190042 A1 | 8/2006 | Stone et al. |
| 2007/0083236 A1 | 4/2007 | Sikora et al. |
| 2008/0065114 A1 | 3/2008 | Stone et al. |
| 2008/0082128 A1 | 4/2008 | Stone |
| 2008/0091237 A1 | 4/2008 | Schwartz et al. |

FOREIGN PATENT DOCUMENTS

| | | |
|---|---|---|
| EP | 0598219 | 5/1994 |
| EP | 0632999 | 1/1995 |
| EP | 0315371 | 5/1999 |
| EP | 0913123 | 5/1999 |
| EP | 1013229 | 6/2000 |
| EP | 0847727 | 2/2004 |
| EP | 1444959 | 8/2004 |
| EP | 1568326 | 10/2007 |
| FR | 2422386 | 4/1978 |
| FR | 2731610 | 9/1996 |
| JP | 54166092 | 11/1979 |

(56) References Cited

FOREIGN PATENT DOCUMENTS

| JP | 54166093 | 11/1979 |
|---|---|---|
| JP | 54176284 | 12/1979 |
| JP | 54178988 | 12/1979 |
| JP | 950770 | 8/1997 |
| WO | 9822047 | 5/1998 |
| WO | 9851241 | 11/1998 |
| WO | 9901084 | 1/1999 |
| WO | 9912480 | 3/1999 |
| WO | 0040159 | 7/2000 |
| WO | 0139671 | 6/2001 |
| WO | 02091959 | 11/2002 |
| WO | 03001893 | 1/2003 |
| WO | 2004037094 | 5/2004 |
| WO | 2005037150 | 4/2005 |

OTHER PUBLICATIONS

Examiner's First Report on Australian Application No. 2007345245, mailed May 22, 2012.
Notice of Reasons of Rejection for Japanese Application No. 2008-518488, mailed Jul. 10, 2012.
Notice of Reasons of Rejection for Japanese Application No. 2009-530498. mailed Jun. 19, 2012.
Office Action issued in U.S. Appl. No. 10/358,252, dated Oct. 13, 2006.
Office Action issued in U.S. Appl. No. 10/358,252, dated May 28, 2009.
Office Action issued in U.S. Appl. No. 10/358,252, dated Dec. 24, 2009 D.
Office Action issued in U.S. Appl. No. 10/358,252, dated Feb. 15, 2011.
Office Action issued in U.S. Appl. No. 10/358,252, dated Oct. 18, 2011.
Office Action issued in U.S. Appl. No. 11/165,551, dated Jun. 2, 2009.
Office Action issued in U.S. Appl. No. 11/535,868, dated May 22, 2009.
Office Action issued in U.S. Appl. No. 11/535,868, dated Mar. 14, 2011.
Office Action issued in U.S. Appl. No. 11/535,868, dated Mar. 24, 2010.
Office Action issued in U.S. Appl. No. 12/684,722, dated Feb. 7, 2012.
Office Action issued in U.S. Appl. No. 12/684,752, dated Jan. 25, 2012.
Communication Pursuant to Article 94(3) EPC for European Application 04708599.8,dated Feb. 18, 2008.
Communication Pursuant to Article 94(3) EPC for European Application 04708599.8,dated Apr. 30, 2009.
Communication Pursuant to Article 94(3) EPC for European Application 04708599.8,dated Feb. 28, 2011.
Annex to Form PCT/ISA/206 Communication Relating to the Results of the Partial International Search (6 pgs) Jul. 30, 2004.
PCT/US2006/024752 International Preliminary Report on Patentability dated Jan. 10, 2008.
PCT/US2006/024752 International Report and Written Opinion dated Nov. 7, 2006.
PCT/US2007/076348 International Search Report and Written Opinion dated Jun. 20, 2008.
PCT/US2004/003528 International Search Report mailed Jul. 30, 2004, 6 pages.
Notice of Reasons of Rejection for Japanese Application No. 2008-518488, mailed Feb. 7, 2012.
Non-Final Office Action mailed Mar. 31, 2009 for U.S. Appl. No. 10/918,445.
Annex to Form PCT/ISA/206 Communication Relating to the Results of the Partial International Search (6 pgs).
PCT/US2004/003258 Annex to Form PCT/ISA/203 Communication Relating to the Results of the Partial International Search, mailed Jul. 30, 2004, 6 Pages.
PCT/US2004/003528 International Search Report, mailed Oct. 21, 2004, 10 pages.
PCT/US2007/076348 International Search Report and Written Opinion, dated Jun. 20, 2008.
Unicom Surgical Sutures & Suture Needles, Suture Needles Information:, 2005.
Office Action U.S. Appl. No. 10/278,474 dated Dec. 29, 2008, 9 pages.
Office Action U.S. Appl. No. 10/358,252 dated Oct. 5, 2005, 7 pages.
Office Action U.S. Appl. No. 10/358,252 dated Feb. 8, 2006, 6 pages.
Office Action U.S. Appl. No. 10/358,252 dated Oct. 13, 2006, 7 pages.
Office Action U.S. Appl. No. 10/358,252 dated Apr. 4, 2007, 6 pages.
Office Action U.S. Appl. No. 10/358,252 dated Jun. 4, 2007, 6 pages.
Office Action U.S. Appl. No. 10/358,252 dated Nov. 20, 2007, 7 pages.
Office Action U.S. Appl. No. 10/358,252 dated May 14, 2008, 8 pages.
Office Action U.S. Appl. No. 10/358,252 dated Dec. 2, 2008, 7 pages.
Office Action U.S. Appl. No. 10/918,445 dated Jul. 24, 2008, 16 pages.
U.S. Appl. No. 60/114,170, filed Dec. 30, 1998; Schwartz et al.
Office Action from European Serial No. 01981796.4 mailed Apr. 21, 2005.
PCT/US2006/024752 International Search Report and Written Opinion, dated Nov. 7, 2006.
PCT /US2006/0247 52 International. Preliminary Report on Patentability, dated Jan. 10, 2008.
Office Action dated Feb. 25, 2008 in U.S. Appl. No. 11/165,551, 15 pages.
Office Action dated Aug. 14, 2008 in U.S. Appl. No. 10/27,474 pages, 14 pages.
Office Action dated Oct. 28, 2008 in U.S. Appl. No. 11/165,551, 13 pages.
Office Action dated May 23, 2008 in U.S. Appl. No. 11/535,868, 14 pages.
Office Action dated Nov. 12, 2008 in U.S. Appl. No. 11/535,868, 18 pages.
Office Actiom dated May 25, 2006—in U.S. Appl. No. 10/918,445; 42, pages.
Office Action dated Oct. 12, 2006 in U.S. Appl. No. 10/918,445, 25 pages.
Office Action dated Mar. 6, 2007 in U.S. Appl. No. 10/918,445, 11 pages.
Office Action dated Jun. 27, 2007 in U.S. Appl. No. 10/278,474, 13 pages.
Office Action dated Aug. 307, 2007 in U.S. Appl. No. 10/278,474, 10 pages.
Office Action dated Dec. 28, 2007 in U.S. Appl. No. 10/918,445, 12 pages.
Office Action dated Jan. 22, 2008 in U.S. Appl. No. 10/278,474, 10 pages.
Thal, R. "A Knotless Suture Anchor & Method for Arthroscopic Bankart Repair Introduction," Poster Board No. 296 at the 1999 Annual Meeting of the American Academy of Orthopaedic Surgeons.
Thal, R. "A Knotless Suture Anchor: Technique for Use in Arthroscopic Bankart Repair," undated.

* cited by examiner

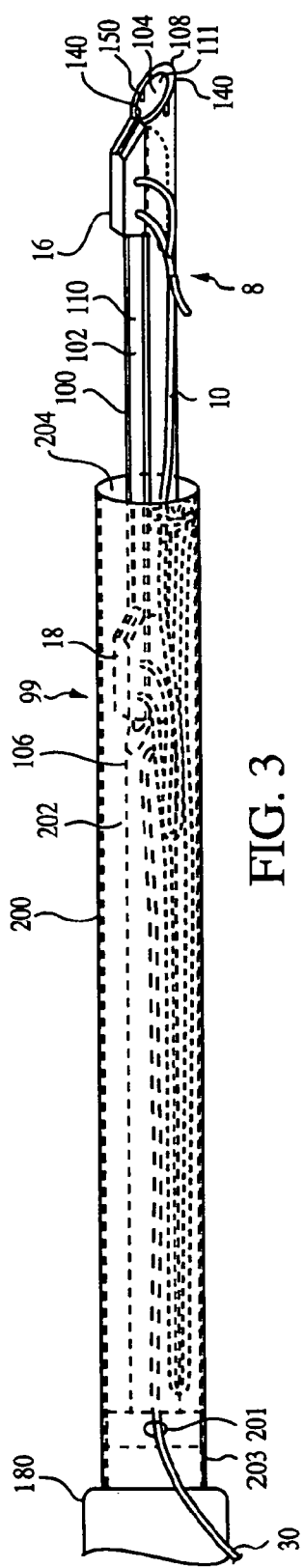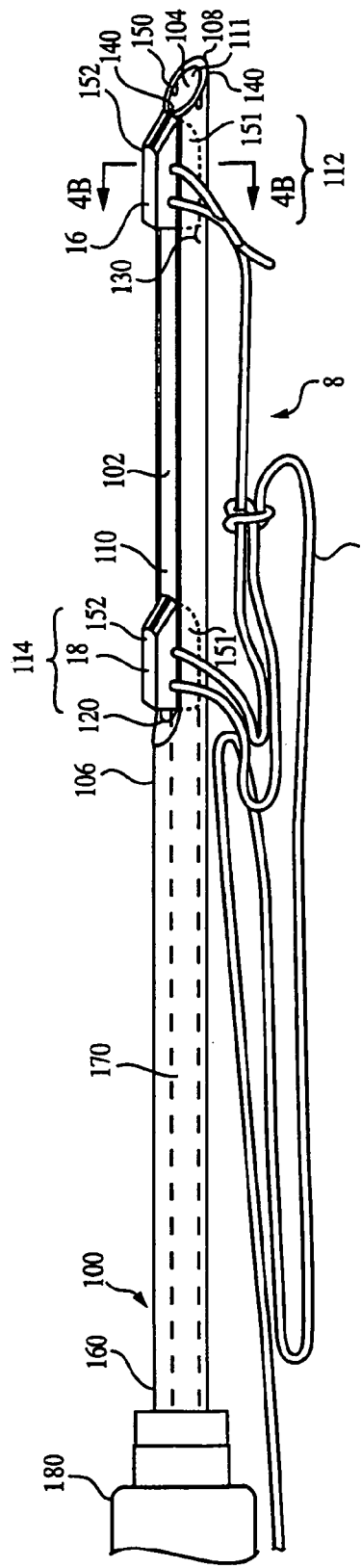
FIG. 3
FIG. 4

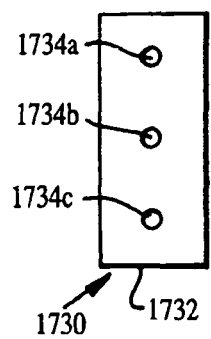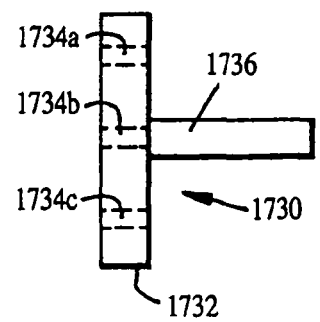
FIG. 28A  FIG. 28B
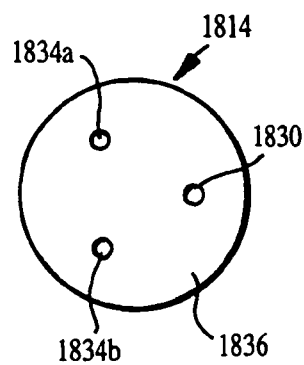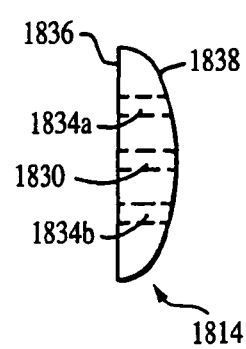
FIG. 28C  FIG. 28D

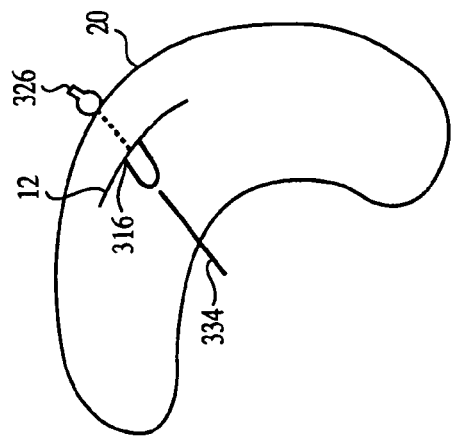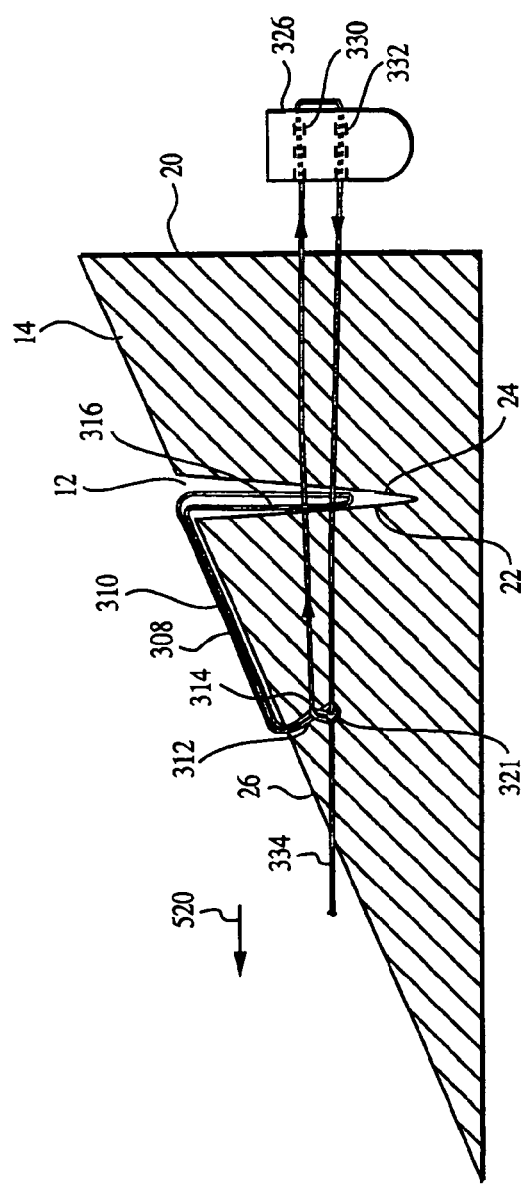
FIG. 36
FIG. 35

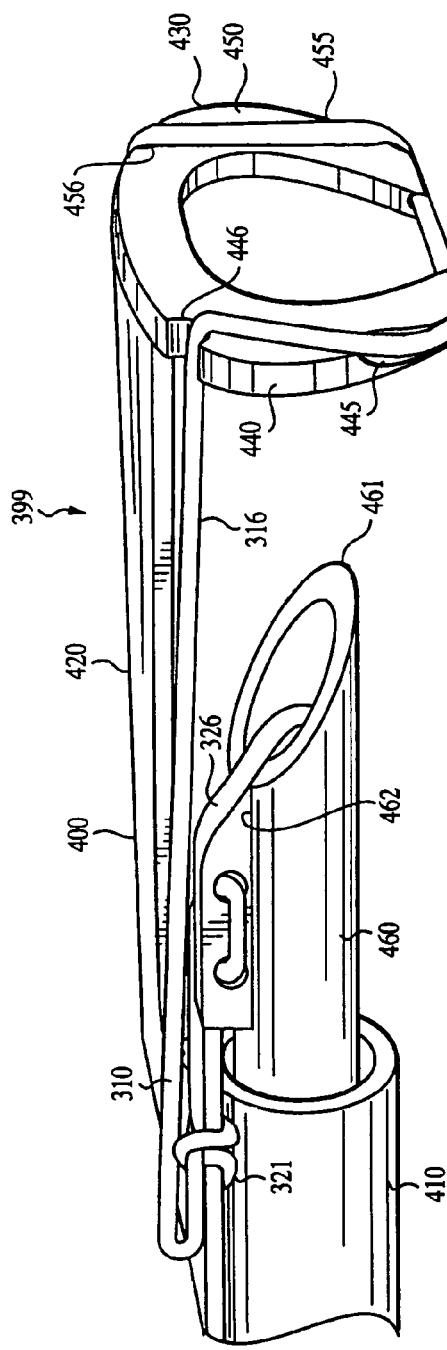
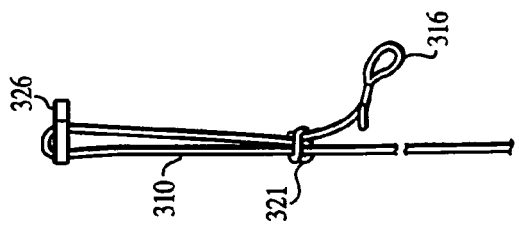
FIG. 37B
FIG. 37C

CLOSURE DEVICE AND METHOD FOR TISSUE REPAIR

CROSS REFERENCE TO RELATED APPLICATIONS

This application is a continuation of U.S. patent application Ser. No. 13/944,682, filed Jul. 17, 2013, entitled CLOSURE DEVICE AND METHOD FOR TISSUE REPAIR (issued on Aug. 27, 2014 as U.S. Pat. No. 8,834,524), which is a continuation of U.S. application Ser. No. 11/025,837, filed Dec. 30, 2004, entitled: CLOSURE AND METHOD FOR TISSUE REPAIR (issued on Jul. 31, 2013 as U.S. Pat. No. 8,512,375), which is a continuation of U.S. application Ser. No. 09/704,926, filed Nov. 2, 2000, entitled CLOSURE DEVICE FOR AND METHOD FOR TISSUE REPAIR (issued on Dec. 6, 2006 as U.S. Pat. No. 7,153,312), which is a continuation-in-part of U.S. application Ser. No. 09/453,120, filed Dec. 2, 1999, entitled WOUND CLOSURE DEVICES AND METHODS now abandoned, all of which are incorporated herein by reference.

BACKGROUND

The invention relates to a closure device and method for tissue repair.

Fibrous tissue wounds, such as muscle, ligament, and cartilage tears, can be repaired arthroscopically using sutures. Traditionally, to close a fibrous tissue wound, a surgeon would insert two suture needles into the tissue with sutures attached, thread the sutures across the wound, and then tie knots to fix the free ends of the sutures within the tissue.

To simplify the wound closure procedure and to improve fixation, various types of suture anchors have been developed. One example of a suture anchor is disclosed in Hayhurst, U.S. Pat. No. 4,741,330, which is incorporated herein by reference. In Hayhurst, one end of a suture is fixed to a resiliently deformable, bar-shaped suture anchor. The anchor is loaded into the bore of a hollow needle and deployed into or against the fibrous tissue. The surgeon then threads the suture across the wound and tensions a free end of the suture to pull the wound closed. When the surgeon tensions the suture, the bar in the anchor becomes oriented transversely to the suture hole, anchoring the suture in place.

SUMMARY

According to one aspect of the invention, in general, the invention features a wound closure device that includes a first anchor, a second anchor, and a flexible member that connects the first anchor to the second anchor. The flexible member is movably attached to the second anchor, such that pulling on a free end of the flexible member shortens a length of the flexible member between the first and second anchors.

Embodiments of this aspect of the invention may include one or more of the following features.

The movable attachment of the flexible member to the second anchor allows the length of the flexible member between the first and second anchors to be shortened, but not lengthened.

The movable attachment can be a knot formed in the flexible member at the second anchor. The knot includes, e.g., a first portion of the flexible member that forms a loop, and a second portion (which might include the free end) that passes over a surface of the second anchor and through the loop. The surface can be, e.g., an exterior surface of the second anchor.

Pulling on the free end of the flexible member in one direction causes the flexible member to slide through the loop, but pulling on the flexible member in an opposite direction causes the loop to press the second portion against a compression surface of the second anchor, resisting increase in the length of the flexible member between the first and second anchors. The loop can be disposed within a partially enclosed region of the second anchor.

The second anchor can include a first section that defines a plurality of holes through which the first portion of the flexible member passes to form the loop. A second section of the second anchor defines a passage that connects to the partially enclosed region, and the free end of the suture passes through this passage.

The second anchor can include a rounded body and an appendage attached to the rounded body, where the rounded body and the appendage define a partially enclosed region therebetween. At least a portion of the flexible member passes through the partially enclosed region. In addition, the flexible member might wrap around the rounded body.

The rounded body can have a generally cylindrical shape, sized to fit within the bore of a hollow needle, and an axial groove. The groove extends across an axial length of the rounded body. The cross-sectional shape of the rounded body can be, e.g., a rectangle, an L, or a D.

The second anchor can also have a generally hemispherical shape, a generally crescent shape, or a T-shape. The crescent-shaped anchor can have sharp tip configured to penetrate tissue.

The second anchor defines a through-hole through which the flexible member passes. In addition, the device can also include a second flexible member that passes through the through-hole, where the second flexible member has a thickened portion that has a width greater than a width of the through-hole, such that the thickened portion cannot pass through the through-hole.

The first anchor includes, e.g., a generally cylindrical body sized and shaped to fit within the bore of a hollow needle, and a projection, such as a longitudinal fin, extending from the cylindrical body. Alternatively, the first anchor can have a button shape. The first anchor can define a hole for passage of the flexible member therethrough, and the flexible member can be fixed to the first anchor.

The flexible member can be a suture.

The wound closure device further includes a retaining element coupled to the flexible member. The retaining element is slidably received by the flexible member and acts to limit loosening of the flexible member relative to the second fixation member. Alternatively, the retaining element is movable relative to the second fixation member and acts to limit loosening of the flexible member relative to the second fixation member.

In another aspect, the invention features a wound closure kit that includes an open-tipped needle and first and second anchors connected by a flexible member disposed within a bore of the needle.

Embodiments of this aspect of the invention may include one or more of the following features.

The needle can define a longitudinal slit, and the first anchor can include a projection that protrudes through the slit. The second anchor can also include an appendage that protrudes through the slit, and the flexible member can be attached to the appendage. The flexible member can be fixed to the first anchor, but movably attached to the second anchor.

In another aspect, the invention features a method of closing a tissue wound. The method includes: (a) providing a wound closure device that has a first anchor, a second anchor, and a flexible member movably attached to the second anchor; (b) positioning the first anchor against tissue; (c) passing the flexible member across the wound; (d) positioning the second anchor against tissue; and (e) pulling on a free end of the flexible member to shorten a length of the flexible member between the first and second anchors, thereby closing the wound.

This aspect of the invention may include one or more of the following features.

The flexible member can be slidably attached to the second anchor by a one-way knot, such that after completion of the pulling step, the length of the flexible member between the first and second anchors remains shortened. Part of the one-way knot can be disposed within a partially enclosed region of the second anchor. The partially enclosed region can be located such that during the pulling step, the portion of the one-way knot disposed within the partially enclosed region avoids contact with tissue.

The first positioning step can include positioning the first anchor on a first side of the wound. The passing step can include passing the flexible member from the first side to a second side of the wound, engaging tissue on the second side, and returning the flexible member to the first side. The second positioning step can include positioning the second anchor on the first side of the wound.

The first and second anchors can initially be disposed, at least partially, within the bore of a hollow, open-tipped needle. The first anchor can include a section that protrudes through a slit in the needle, and the first positioning step can include engaging the projection with tissue to remove the first anchor from the bore.

The providing step can include providing a device in which the flexible member passes through a through-hole in the second anchor, and the device further includes a second flexible member that also passes through the through-hole. The second flexible member has a thickened portion that is wider than the through hole. The method further includes pulling the second flexible member until the thickened portion wedges into the through hole.

In another aspect, the invention features a method of repairing a tear in a meniscus. The method includes: (a) providing a tear closing device having a first anchor, a second anchor, and a flexible member movably attached to the second anchor; (b) positioning the first anchor against the meniscus; (c) passing the flexible member across the tear; (d) positioning the second anchor against the meniscus; and (e) pulling on a free end of the flexible member to shorten a length of the flexible member between the first and second anchors, thereby closing the tear.

Embodiments of this aspect of the invention can include one or more of the following features.

The first positioning step can include positioning the first anchor against an external surface of the meniscus, on a first side of the tear, the passing step can include passing the flexible member from the first side to a second side of the tear, engaging tissue on the second side, and returning the flexible member to the first side, and the second positioning step can include positioning the second anchor against the external surface. Alternatively, the first and second anchors can be positioned against external surfaces of the meniscus on opposite sides of the tear.

According to another aspect of the invention, a surgical method includes positioning a fixation member relative to tissue, moving a flexible member coupled to the fixation member relative to the fixation member to bring two tissue surfaces together, and moving a retaining element coupled to the flexible member relative to the fixation member. The retaining element acts to limit loosening of the flexible member relative to the fixation member.

Embodiments of this aspect of the invention may include one or more of the following features.

The step of moving the flexible member comprises pulling the flexible member. The step of moving the flexible member also accomplishes the step of moving the retaining element, which is, for example, a slip knot. Alternatively, the step of moving the retaining element includes moving the retaining element relative to the flexible element. The retaining element is, for example, a friction element which permits sliding of the retaining element relative to the flexible element in only one direction. In another illustrated embodiment the retaining element is in the form of an overhand knot, and the method includes advancing the overhand knot along the flexible element. In another illustrated embodiment, the retaining element is in the form of a Chinese trap.

In an exemplary embodiment, the step of moving the flexible member includes pulling on only one end of the flexible member.

In another illustrated embodiment, the method includes positioning a second fixation member relative to the tissue. The second fixation member is coupled to the flexible member, either movably or fixedly. The step of moving the flexible member includes, for example, pulling on two ends of the flexible member or pulling on only one end of the flexible member.

The step of positioning the fixation member includes positioning the fixation member on an outer surface of the tissue, and the two tissue surfaces brought together are both soft tissue. Alternatively, the fixation member is positioned in a bone hole, and one of the two tissue surfaces brought together is bone and the other soft tissue.

In another illustrated embodiment, the step of positioning the fixation member includes passing the fixation member through a loop of the flexible member. The loop is positioned within a tear in soft tissue.

According to another aspect of the invention, a method for repairing a tear in soft tissue includes advancing a fixation member coupled to a flexible member through tissue on either side of the tear and through a loop of the flexible member, and tensioning the flexible member to bring two tissue surfaces on either side of the tear together.

Embodiments of this aspect of the invention may include one or more of the following features. The loop is positioned within the tear. The method includes pulling an end of the flexible member to bring the two tissue surfaces together. The fixation member is in the form of a barbed member.

According to another aspect of the invention, an apparatus for repairing a tear in soft tissue includes at least two fixation members, a flexible member substantially immovably secured to the first fixation member and movably coupled to the second fixation member, and a retaining element coupled to the flexible member. The retaining element is movable relative to the second fixation member and acts to limit loosening of the flexible member relative to the fixation member.

According to another aspect of the invention, an apparatus for repairing a tear in soft tissue includes at least two fixation members, a flexible member substantially immovably secured to the first fixation member and movably coupled to the second fixation member, and a retaining element coupled to the flexible member. The retaining element is slidably received by the flexible member and acts to limit loosening of the flexible member relative to the fixation member.

According to another aspect of the invention, an apparatus for repairing a tear in soft tissue includes a fixation member, and a flexible member movably coupled to the fixation member. A first end of the flexible member is looped back and secured to the flexible member to form a loop. The loop is remote from the fixation member.

According to another aspect of the invention, a flexible member holder includes a shaft, a first tine at an end region of the shaft defining a first region for receiving a first portion of a loop of a flexible member, and a second tine at the end region of the shaft defining a second region for receiving a second portion of the loop of the flexible member.

Embodiments of this aspect of the invention may include one or more of the following features. The shaft is a tube. The first and second regions are grooves.

According to another aspect of the invention, a device for repairing a tear in a tissue includes a needle having a distal region defined between two holding elements, and a proximal region. A first fixation member is positioned within the distal region and a second fixation member is positioned within the proximal region. A flexible member is coupled to the first and second fixation members.

Embodiments of this aspect of the invention may include one or more of the following features. A first of the holding elements is a crimp in the needle in the distal region, and the second holding element is a dimple or ramp extending into a lumen of the needle. The needle wall has a slot and the fixation members extend through the slot. The needle is sized to fit into an end of a protector tube. A push pin is sized to fit inside the needle.

Embodiments of the invention may include one or more of the following advantages. The first and second anchors can be deployed using a single hollow needle, rather than two separate needles. After deploying a fixation member or anchor, the surgeon need not tie an additional knot. The length of a flexible member coupled to the fixation member can be adjusted after deploying the fixation member, allowing a surgeon to set the tension in the flexible member to a desired level. The length of a flexible member spanning across a tear in tissue can be shortened to close the tear by tensioning the flexible member with no additional manipulation being required to limit loosening of the flexible member.

Since the device uses a flexible member, such as a suture, to close the tissue wound, rather than inflexible staples or tacks, the tissue is not significantly damaged when it expands and contracts. For example, if the soft tissue is a meniscus, the fixation members do not damage the meniscal tissue when the knee moves.

The details of one or more embodiments of the invention are set forth in the accompanying drawings and the description below. Other features, objects, and advantages of the invention will be apparent form the description and drawings, and from the claims.

DESCRIPTIONS OF DRAWINGS

FIG. 3 is a perspective view of a delivery device for inserting the closure device of FIG. 1 into soft tissue;

FIG. 4 is a perspective view of the delivery device of FIG. 3 shown with an outer sheath removed;

FIG. 28A is a top view of a T-shaped second suture anchor;

FIG. 28B is a side view of the T-shaped suture anchor of FIG. 28A;

FIG. 28C is a front view of a crescent-shaped second suture anchor;

FIG. 28D is a side view of the crescent-shaped suture anchor of FIG. 13C;

FIG. 35 shows the closure device of FIG. 34 in use prior to securing the closure device in place;

FIG. 36 is a top view of the closure device of FIG. 34, shown after securing the closure device in place;

FIG. 37B is a perspective view similar to that of FIG. 37A shown with the closure device of FIG. 34;

FIG. 37C is an illustration of the closure device of FIG. 34;

DETAILED DESCRIPTION

Figure 1:
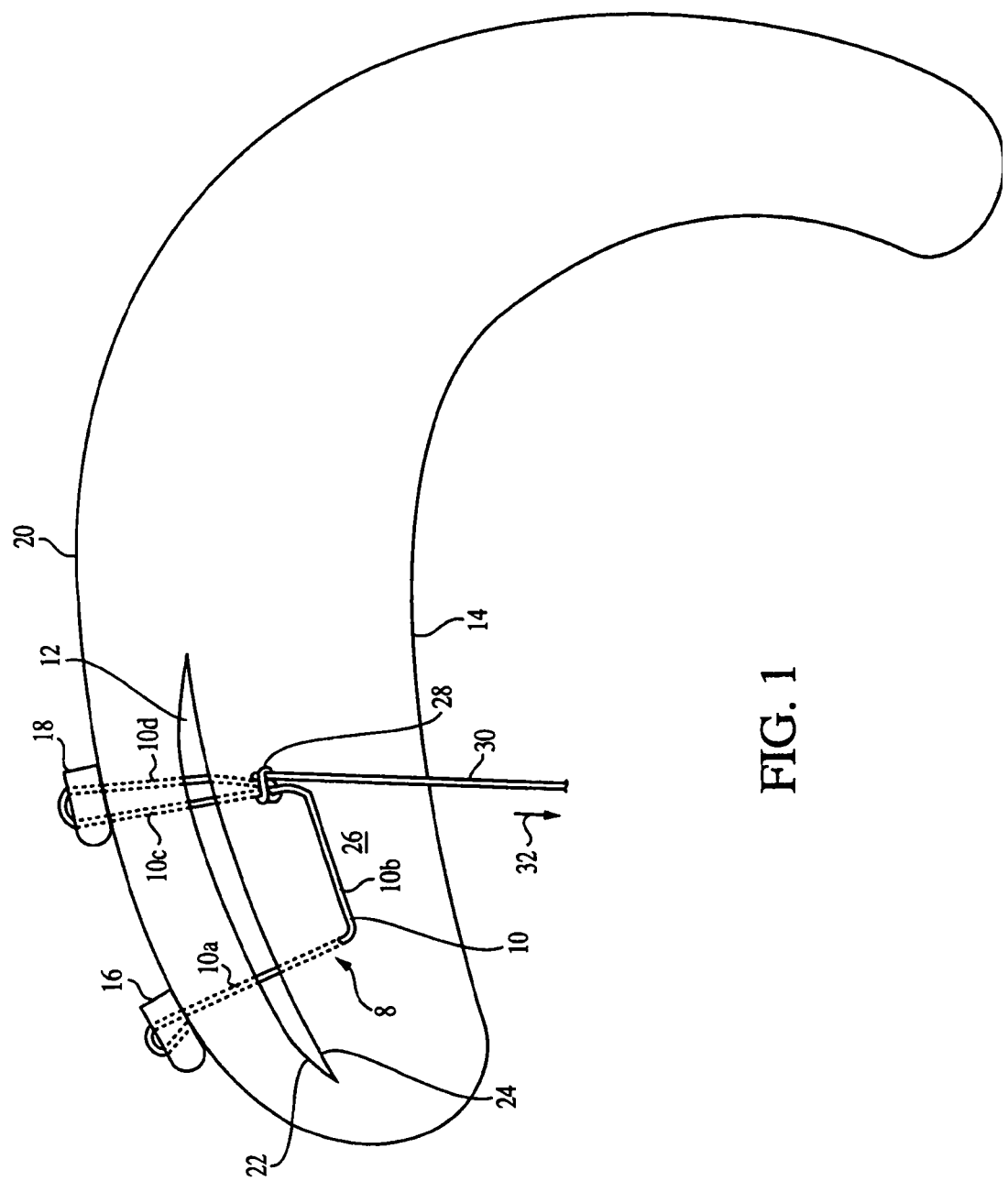
FIG. 1 is an illustration of a closure device according to the invention, shown mending a tear in soft tissue.

Referring to FIG. 1, a closure device 8 for mending a tear 12 in soft tissue 14, e.g., meniscus of the knee joint, includes a flexible member, e.g., suture 10, coupled to a first fixation member 16 and a second fixation member 18. Suture 10 is fastened to fixation member 16 to limit movement of suture 10 relative to fixation member 16, while suture 10 is movable relative to fixation member 18.

Figure 10:
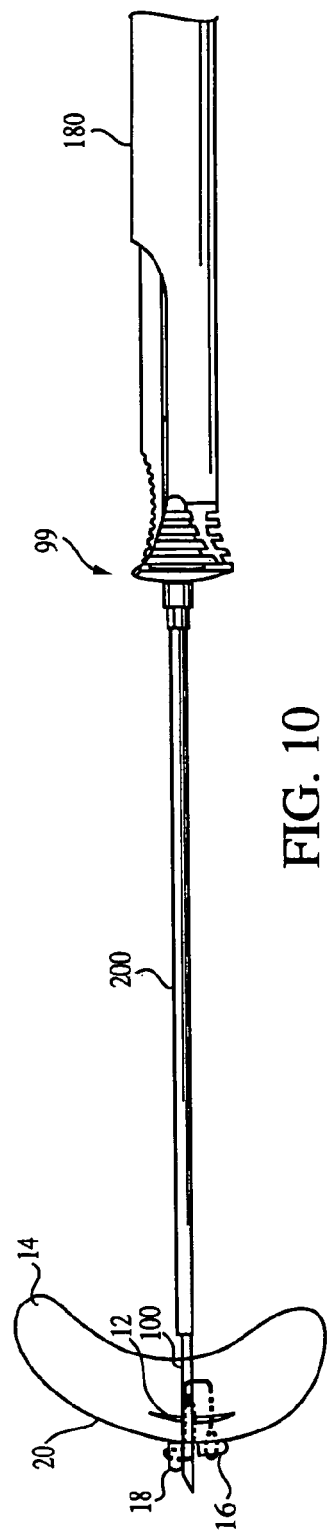

When implanted in the knee joint, fixation members 16 and 18 lie on a surface 20 of tissue 14, for example, the outer surface of the meniscus. Suture 10 has a first suture length 10a extending from first fixation member 16 through tissue 14, traversing tear 12, and emerging at a surface 26 of tissue 14; a second suture length 10b extending across surface 26; a third suture length 10c extending back through tissue 14, traversing tear 12 at a location spaced from first length 10a, and emerging at tissue surface 20 where suture 10 loops through second fixation member 18; and a fourth suture length 10d extending from second fixation member 18 through tissue 14, traversing tear 12, and emerging at surface 26. Suture 10 has a free end 30 which the surgeon pulls, in the direction of arrow 32, to bring sides 22, 24 of tear 12 together into juxtaposition (as shown in FIG. 10).

As described further below, suture portion 10c and suture portion 10d are tied together prior to implantation of device 8 to form a retaining element in the form of a slip knot 28 that allows suture 10 to be pulled in the direction of arrow 32, but does not allow tension on suture 10 to pull suture 10 in the opposite direction, which would allow tear 12 to re-open.

Figure 2A:
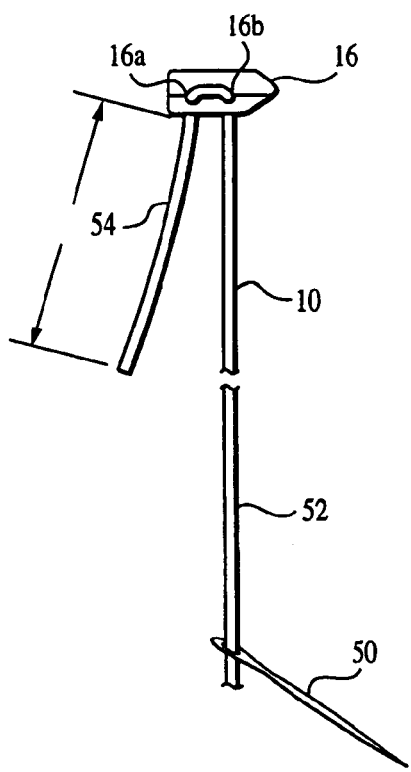
FIGS. 2A-2I show a method of tying a slip knot in suture of the closure device of FIG. 1.
Figure 2B:
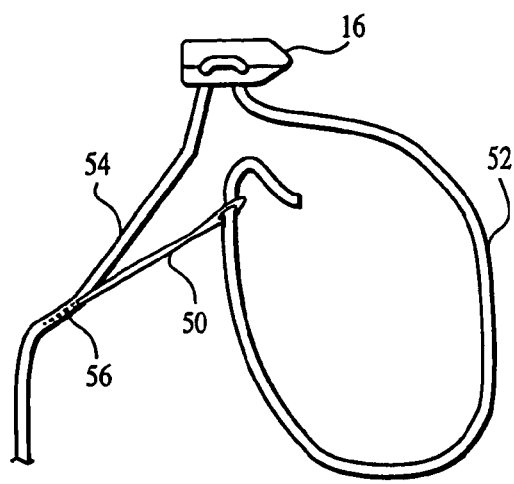
Figure 2C:
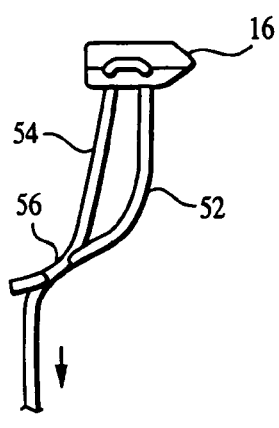
Figure 2D:
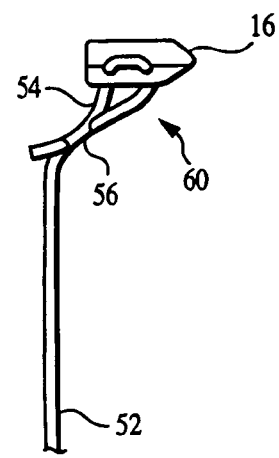

Referring to FIGS. 2A-2I, prior to insertion into tissue 14, suture 10 is attached to fixation members 16, 18 and slip knot 28 is formed. Fixation member 16 defines holes 16a, 16b for receiving suture 10, and fixation member 18 defines holes 18a, 18b for receiving suture 10. As illustrated in FIGS. 2A-2D, suture 10 is attached to fixation member 16 by threading suture 10 through a needle 50, and passing needle 50 and suture 10 through holes 16a, 16b in fixation member 16 (FIG. 2A). Suture 10 now defines a long suture section 15 and a short suture section 54. Long suture section 15 is then attached to short suture section 54 by passing needle 50 and long suture section 15 through short suture section 54 at a region 56 (FIG. 2B). Pulling long suture section 15 away from fixation member 16 (FIG. 2C) then draws region 56 toward fixation member 16 forming a knot 60 (FIG. 2D). Suture 10 is now secured to fixation member 16.

Figure 2E:
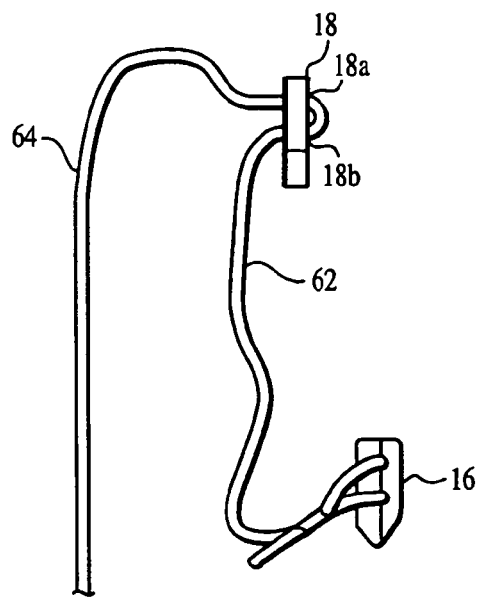
Figure 2F:
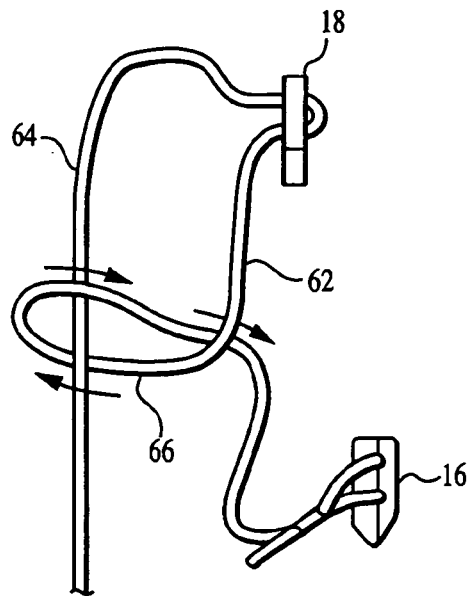
Figure 2G:
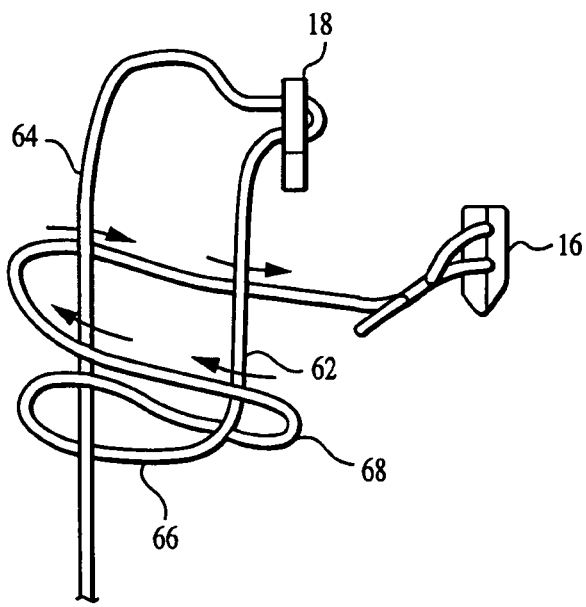
Figure 2H:
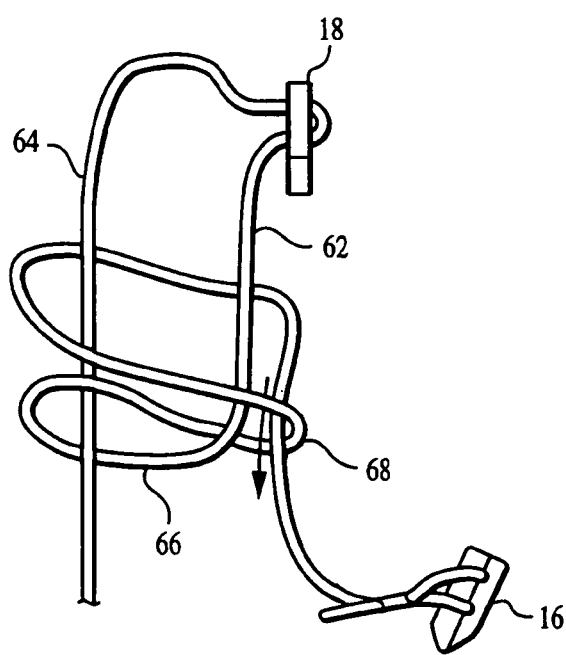
Figure 2I:
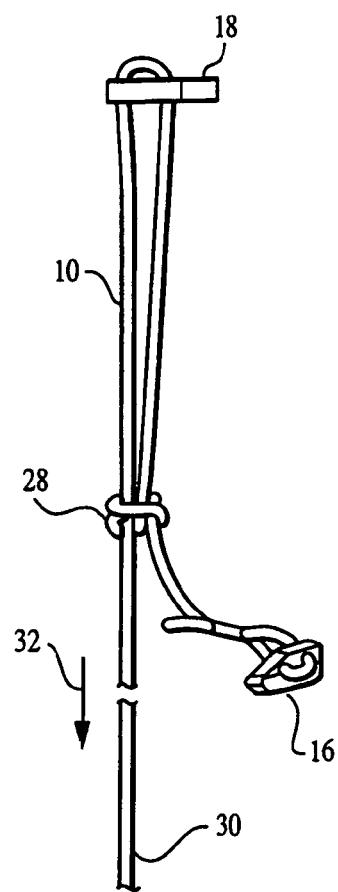

Referring to FIGS. 2E-2I, suture 10 is now attached to fixation member 18 by passing long suture section 15 through holes 18a, 18b in second fixation member 18 (FIG. 2E). Long suture section 15 now defines a first suture length 62 and second suture length 64. Slip knot 28 is formed by passing fixation member 16 under suture length 64, over suture length 64, and under suture length 62, forming a loop 66 (FIG. 2F); then passing fixation member 16 over suture lengths 62 and 64, forming a loop 68 (FIG. 2G); and then passing fixation member 16 under suture lengths 64 and 62 (FIG. 2G), and finally through loop 68 (FIG. 2H). Pulling fixation member 16 relative to fixation member 18 tightens slip knot 28 (FIG. 2I). Pulling free end 30 of suture 10 now acts to slide suture 10 through slip knot 28, while slip knot 28 limits sliding of suture 10 in the opposite direction when suture 10 is under tension.

Referring to FIG. 3, a delivery device 99 for implanting device 8 in tissue 14 includes a sheath 200 and a needle 100. Sheath 200 is preferably formed from plastic, and needle 100 is preferably metal. Needle 100 has an open distal end 111 with a pointed, tissue piercing tip 108. Needle 100 has an inner surface 102 defining a lumen 104 and a slot 110 both extending to open distal end 111. Slot 110 extends from an outer surface 106 of needle 100 to lumen 102. As described further below, needle 100 receives fixation member 16 and 18 within lumen 104 and slot 110 with suture 10 tied to fixation members 16, 18 as illustrated in FIGS. 2A-2I. Sheath 200 defines a lumen 202 which receives needle 100 and device 8 with suture 10 positioned between needle 100 and sheath 200 and extending through a hole 201 defined at a proximal end 203 of sheath 200. Sheath 200 has a distal end 202 from which needle 100 extends.

Figure 4B:
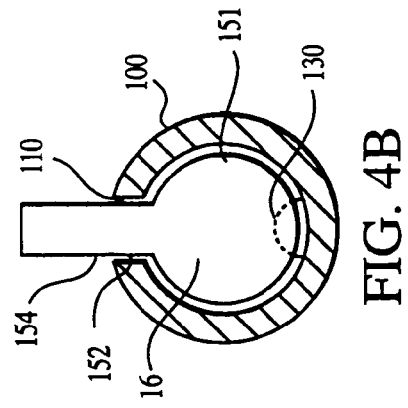
FIG. 4B is a cross-sectional end view of the delivery device of FIG. 4, taken along lines 19B-19B.
Figure 4C:
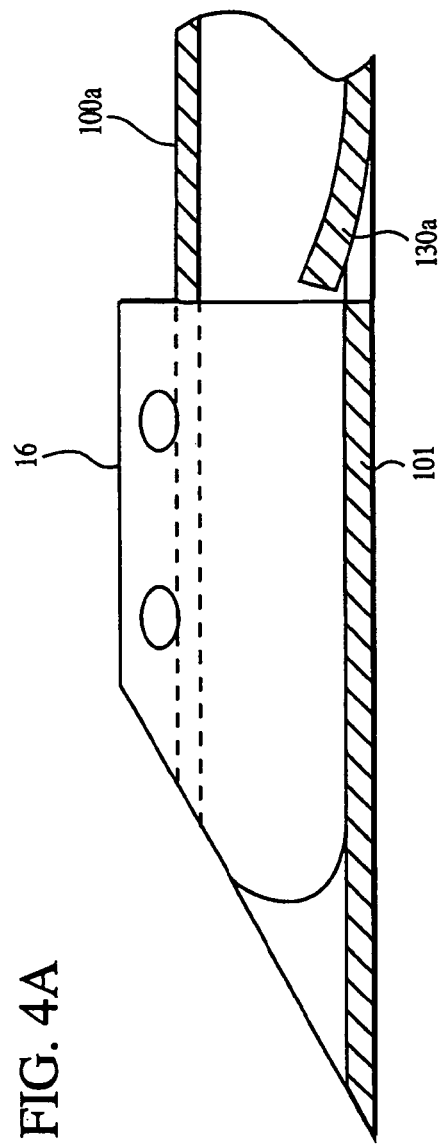
FIG. 4C is a cross-sectional side view of an alternative embodiment of a needle of the delivery device of FIG. 3.
Figure 4A:
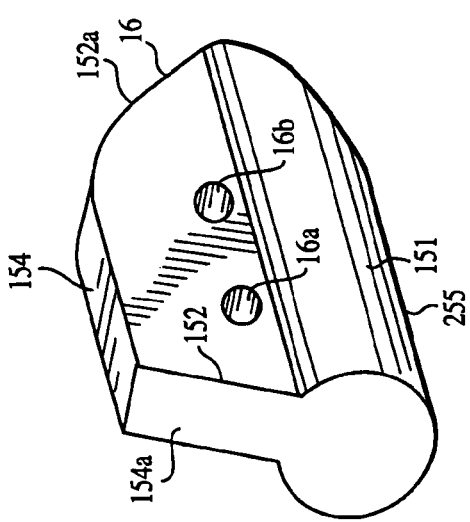
FIG. 4A is a perspective view of a fixation member of the closure device of FIG. 1.

Referring also to FIGS. 4-4B, slot 110 has a proximal, closed end 120 and a distal open end 140. Fixation members 16 and 18 (which are generally described in U.S. Ser. No. 09/453,120, supra) have the same shape with each fixation member including a cylindrical region 151 received within lumen 104 of needle 100, and a fin 115 extending through slot 110 with a portion 154 of fin 115 extending beyond outer surface 106 of needle 100. Fixation member 16 is located at a distal region 112 of slot 110, and fixation member 18 is located at a proximal region 114 of slot 110. Distal end 111 of needle 100 is indented, for example, crimped at 150, and inner surface 102 of needle 100 has a protrusion extending into lumen 104, for example, a dimple 130, near distal end 140. Dimple 130 and crimp 150 are sized to resist unintentional passage of the fixation members either over dimple 130 or through open distal end 111, though only a small force on the fixation members is needed to overcome the resisting load applied to the fixation members by crimp 150 and dimple 130. Fixation members 16, 18 have sloped surfaces 115a which aid in passage through tissue, and a flat surface 154a which aid in retention of the fixation member at their deployment sites.

During manufacturing, to position fixation members 16, 18 in needle 100, after suture 10 is attached to fixation members 16, 18, fixation member 18 is loaded in needle 100 by passing fixation member 18 through distal end 111 and sliding fixation member 18 along lumen 104 and slot 110 to proximal end 120 of slot 110. Fixation member 16 is then loaded in needle 100 by passing fixation member 16 through distal end 111 and positioning fixation member 16 in region 112. Dimple 130 and crimp 150 are then formed. Fixation member 16 is now restrained from unintentional movement in the proximal direction by dimple 130 and in the distal direction by crimp 150. Alternatively, as shown in FIG. 4C, rather than dimple 130, a needle 100a includes a ramp 130a formed by making three slits in a wall 101 of needle 100a and bending a section of the wall toward the inside of the needle.

Figure 5:
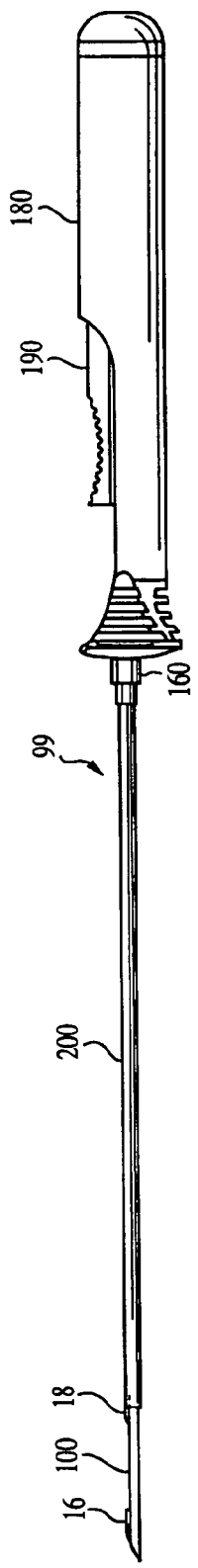
FIG. 5 is side view of the delivery device of FIG. 3.

Referring also to FIG. 5, needle 100 has a proximal end 160 mounted to a handle 180. Located within needle 100, proximal of fixation member 18, is a push rod 170 (FIG. 4) used to advance fixation member 18, as described below. Handle 180 includes an actuating slider 190 attached to push rod 170 for advancing push rod 170. Once device 8 is secured to needle 100, as described above, sheath 200 is placed over needle 100, with the majority of suture 10 located within and protected by sheath 200. Sheath 200 also covers the majority of fixation member 18 and helps keep fixation member 18 in position. Sheath 200 is then secured to handle 180 by an interference fit. The distance needle 100 extends from sheath 200 determines the penetration depth of needle 100 into the tissue. Delivery device 99 is supplied to the surgeon with device 8 pre-loaded in needle 100.

Figure 5A:
FIG. 5A is a side view of a variable length depth stop for use with the delivery device of FIG. 3.

Referring to FIG. 5A, an outer protective tube 200a can be placed over sheath 200. Tube 200a protects the needle tip during shipping. If it is desired to supply the surgeon with a variable length depth stop, tube 200a can be provided with gradations 201. The surgeon scores tube 200a to provide the tube with the desired length for the surgical procedure. Tube 200a is coupled to handle 190 by a loose interference fit to allow the surgeon to remove tube 200a if tube 200a is not being used during surgery.

Figure 5B:
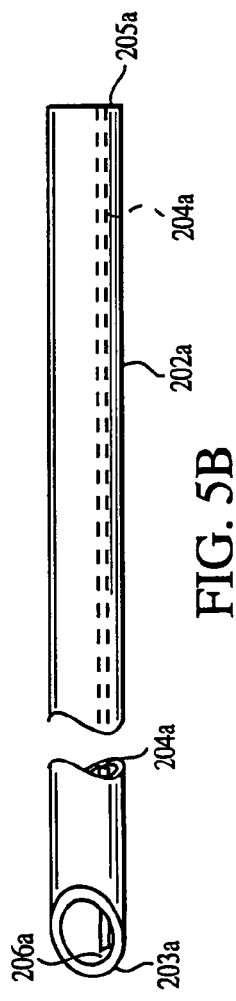
FIG. 5B is a perspective view of a cannula for use with the delivery device of FIG. 3.
Figure 6:
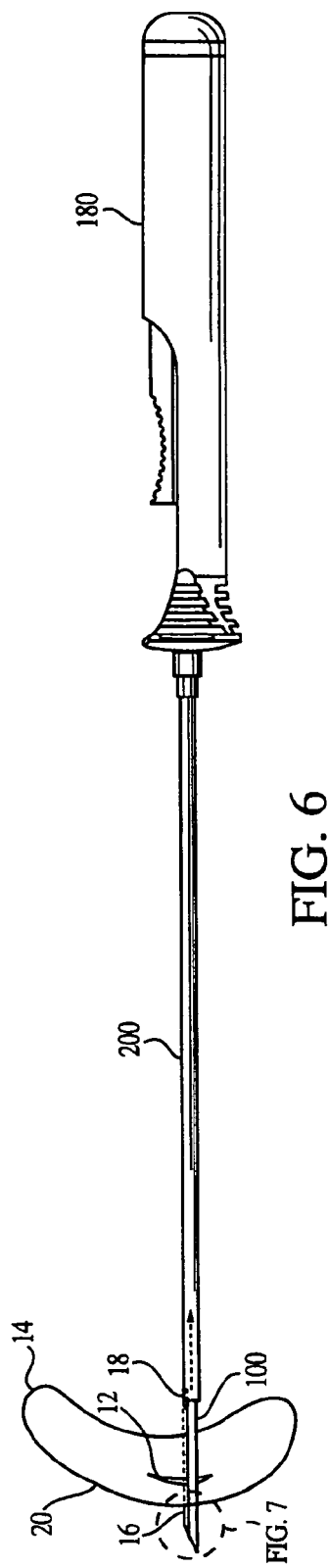
FIGS. 6-11 show the delivery device in use inserting the closure device of FIG. 1 in soft tissue, with FIG. 7 being an exploded view of region 7 of FIG. 6.

Referring to FIG. 5B, to eliminate the need for placement of delivery device 99 through an arthroscopy cannula, a removable cannula 202a, formed, for example, of a plastic material, can be placed over sheath 200. Cannula 202a has a distal, tissue penetrating tip 203a and a slot 204a extending from a proximal end 205a of cannula 202a to within about 0.02 inches of distal tip 203a to define a distal region 206a. Slot 204a permits the removal of cannula 202a from delivery device 99 after placement of the delivery device in the joint. To remove cannula 202a, the surgeon grasps the cannula and moves it laterally relative to sheath 200, until sheath 200 slides through slot 204a. The surgeon then pulls cannula 202a proximally, which breaks cannula region 206a, permitting complete removal of cannula 202a.

Figure 7:
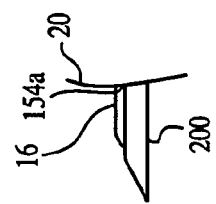
Figure 8:
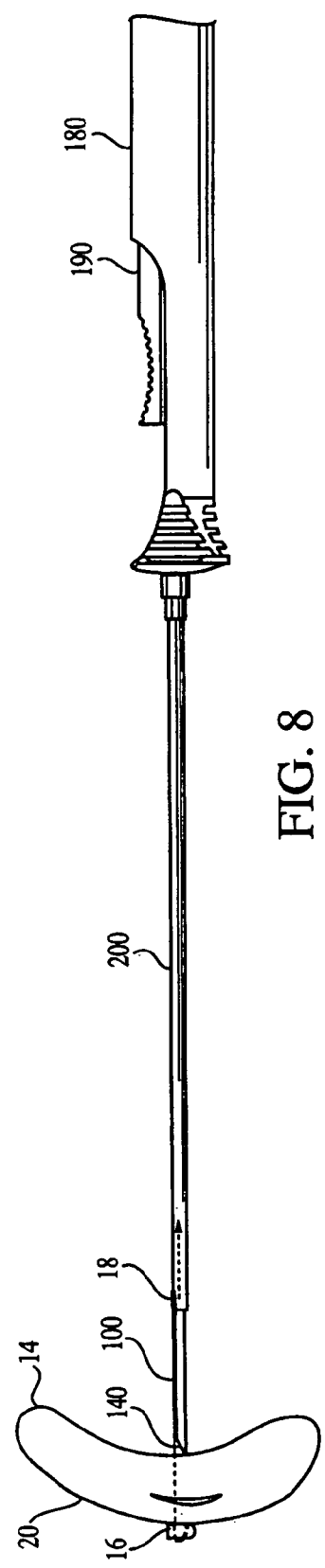

Referring to FIGS. 6-11, in use, preferably under arthroscopic guidance, the user inserts delivery device 99 into, for example, the knee joint, and passes needle 100 through soft tissue 14 and across tear 12, until needle tip 108 and fixation member 16 extend through tissue surface 20. Dimple 130 prevents fixation member 16 from sliding proximally in response to forces acting on fixation member 16 during insertion through tissue 14. Fixation member 16 is now positioned with flat, tissue facing surface 154a of portion 154 of fin 115 extending beyond needle surface 106 engaging tissue surface 20 (FIG. 7). The user then pulls delivery device 99 proximally removing needle 100 from tissue 14 (FIG. 8). The force of the engagement of fixation member 16 with tissue surface 20 during removal of needle 100 overcomes the retention force of crimp 150. Fixation member 16 slides distally out of open end 111 of needle 100 and remains at surface 20. During the retraction of needle 100, a portion of suture 110 with knot 28 is played out of delivery device 99, with suture 10 extending through soft tissue 14 across tear 12.

Figure 9:
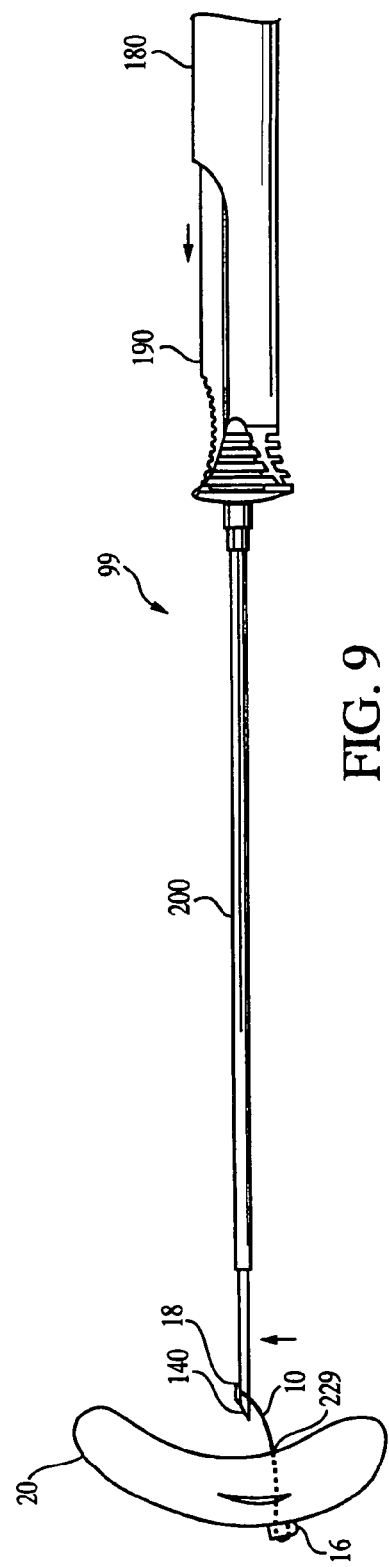
Figure 11:
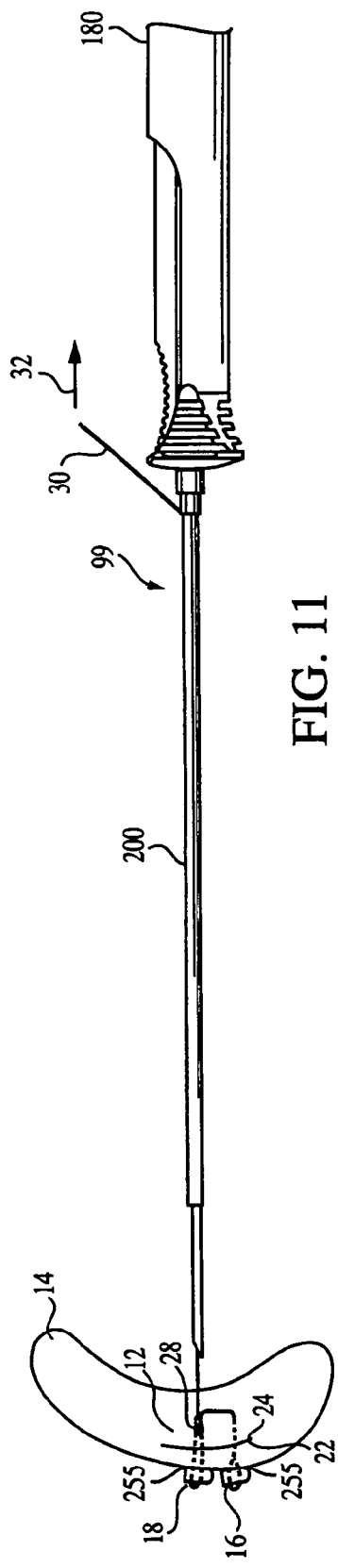

The user then advances slider 190, advancing rod 170 to push fixation member 18 distally, over dimple 130, to reside in region 112 between dimple 130 and crimp 150 (FIG. 9). The user then moves needle 100 to a spaced location to the side of exit point 229 of suture 10 from tissue 14, and re-inserts needle 100 into soft tissue 14, across tear 12, and through surface 20, until needle tip 108 and fixation member 18 extend through tissue surface 20 (FIG. 10). The user then pulls delivery device 99 proximally removing needle 100 from tissue 14 (FIG. 11). The force of the engagement of fixation member 18 with tissue surface 20 during removal of needle 100 overcomes the retention force of crimp 150 such that fixation member 18 slides distally out of open end 111 of needle 100 and remains at surface 20, as described above with reference to fixation member 16.

Free end 30 of suture 10 extends from sheath 200, as shown in FIG. 11. The user grasps free end 30 of suture 10 with forceps or by hand and pulls on free end 30 of suture 10. This shortens the length of suture between fixation members 16 and 18 (suture portions 10a-10c), bringing sides 22, 24 of tear 12 into juxtaposition, as shown in FIG. 11. When free end 30 of suture 10 is pulled, slip knot 28 moves closer to fixation member 18. Depending on the length of suture between fixation members 16 and 18, slip knot 28 will either be on tissue surface 26 or move within tissue 14. Slip knot 28 allows suture 10 to slide in the direction of arrow 32, but does not allow suture 10 to slide in the opposite direction. The tension placed on suture 10 by pulling on the suture relative to fixation members 16, 18, acts to turn the fixation members such that their long sides 255 are in contact with tissue surface 20. Excess suture 10 can then be cut off. Further manipulation of suture 10 is not needed to secure fixation members 16, 18, although the surgeon may wish to provide additional fastening as a back-up securement measure.

Figure 12:
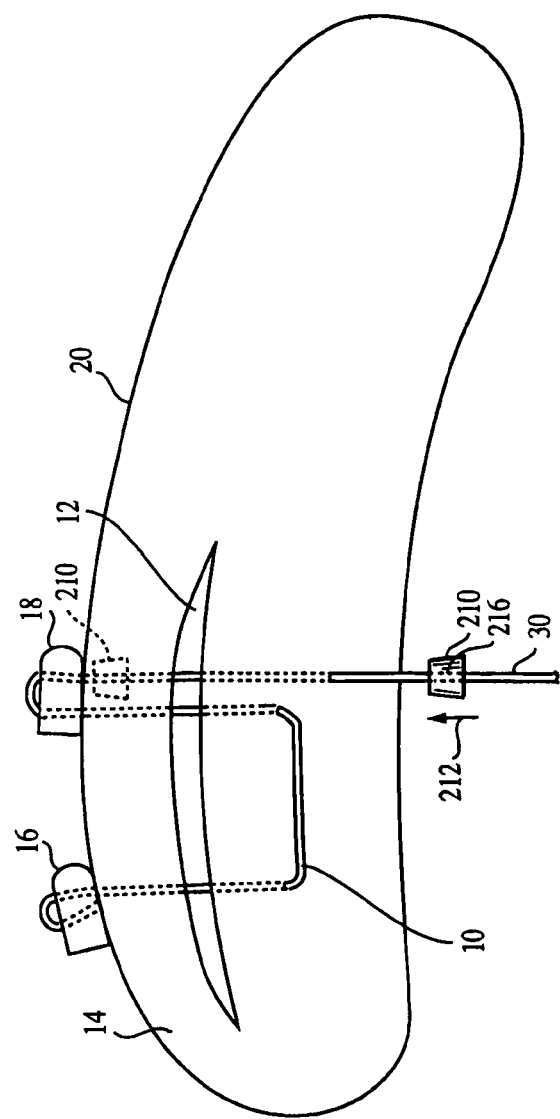
FIG. 12 is an illustration of the closure device of FIG. 1 with an alternative embodiment of a retaining element, shown mending a tear in soft tissue.

Referring to FIG. 12, rather than a slip knot 28 acting as a retaining element allowing suture 10 to be tightened while resisting loosening of suture 10, here, a separate retaining element 210 is positioned on free end 30 of suture 10. While pulling on free end 30, the surgeon advances retaining element 210 through tissue 14, in the direction of arrow 212, until retaining element 210 is positioned against fixation member 18, as shown in dashed line. This action acts to close tear 12 and secure device 8 in place.

Retaining element 210 defines a through bore 216 for receiving suture 10. The material of retaining element 210, e.g., acetal, is selected, and the diameter of through bore 216 is sized relative to suture 10 to provide the desired amount of friction between suture 10 and retaining element 210 for adequate securement. Thus, the user can slide suture 10 in the direction of arrow 212, but adequate friction is provided between suture 10 and retaining element 210 to limit sliding of retaining element 210 in the opposite direction under normal loads in the knee joint.

Figure 12C:
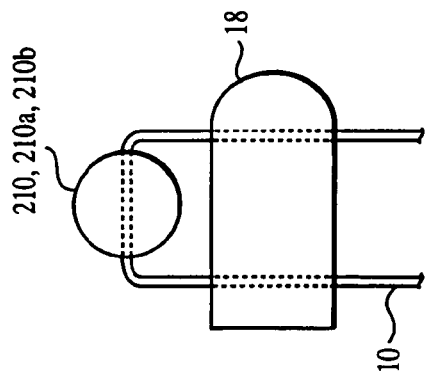
FIG. 12C shows the retaining element of FIG. 12 in an alternative position.
Figure 12B:
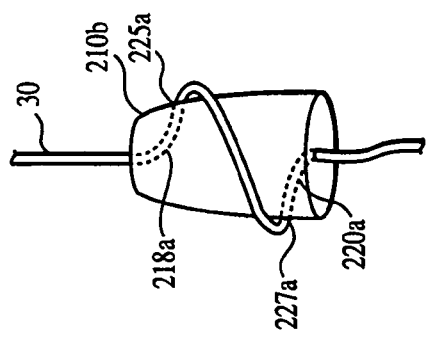
FIGS. 12A and 12B show alternative embodiments of the retaining element of FIG. 11.
Figure 12A:
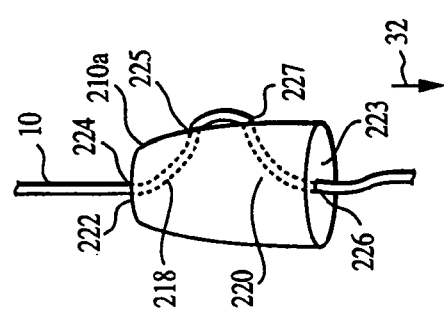

Referring to FIG. 12A, a retaining element 210a defines two angled channels 218, 220 for receiving free end 30 of suture 10. Retaining element 210a has a generally cylindrical surface 221 and ends 222, 223. Channel 218 has a first opening 224 at end 222 and second opening 225 on surface 221. Channel 220 has a first opening 226 at end 223 and a second opening 227 on the same side of surface 221 as channel 218. Suture 10 follows a tortuous path through channel 218, over surface 221 between openings 225 and 227, and then through channel 220 with free end 30 extending from opening 226. The tortuous path aids in securement of device 8.

In FIG. 12B, rather the channel opening on surface 221 being on the same side, a retaining element 210b defines two angled channels 218a, 220a each having a channel end 225a, 227a, respectively, on opposite sides of surface 221. Suture 10 thus wraps part way around element 210b to aid in securement of device 8.

Referring to FIG. 12C, rather than positioning the retaining element on suture 10 after suture 10 exits from fixation member 18, here retaining element 210, 210a, or 210b is positioned along suture 10 between the portions of suture 10 passing through fixation member 18.

Retaining elements 210, 210a, 210b are slidably received on suture 10. In the embodiments of FIGS. 12-12B, the retaining element slides over suture 10, changing position relative to fixation member 18, while in the embodiment of FIG. 12C, suture 10 slides within the retaining element with the position of the retaining element being relatively unchanged relative to fixation member 18.

Figure 13:
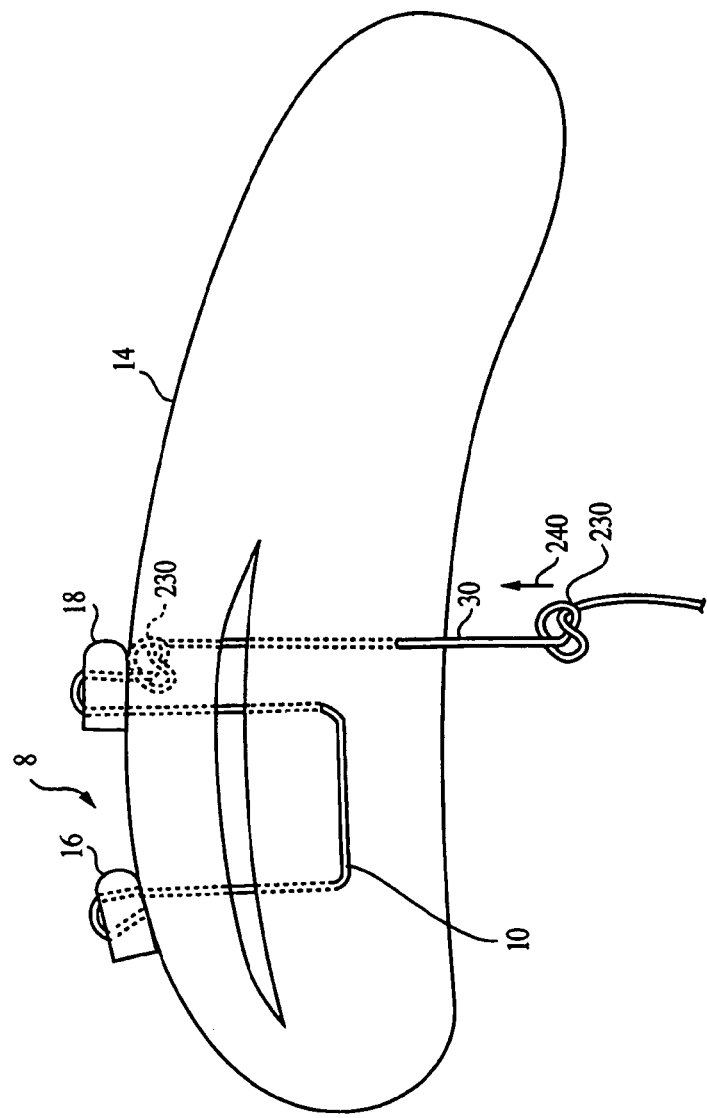
FIG. 13 shows an additional alternative embodiment of a retaining element in the form of an overhand knot.
Figure 13B:
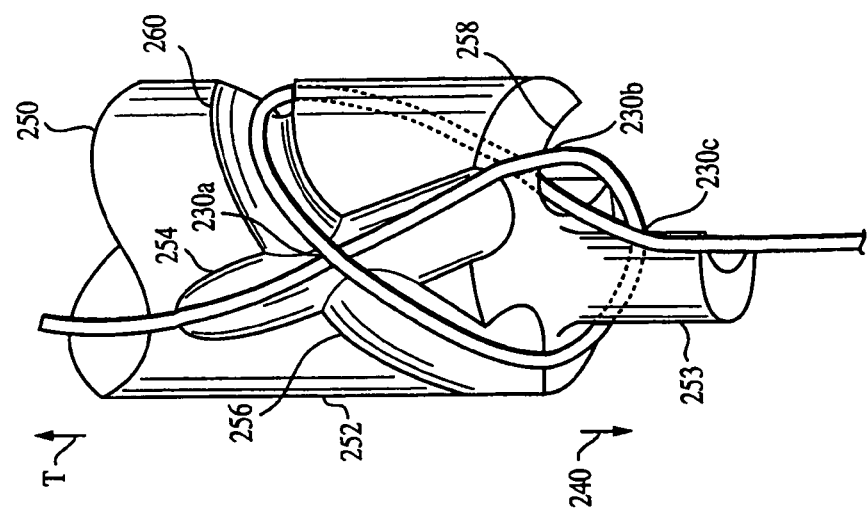
FIGS. 13A and 13B show an overhand knot and a knot pusher for advancing the overhand knot of FIG. 13.
Figure 13A:
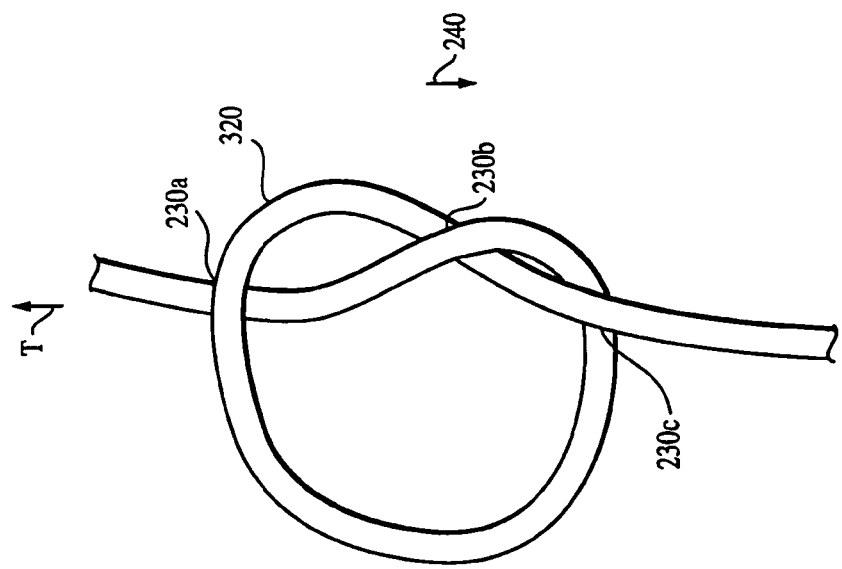

Referring to FIG. 13, device 8 can be secured to tissue 14 using a simple overhand knot 230. Knot 230 is first tied in free end 30 of suture 10 and pushed, in the direction of arrow 240, through tissue 14 and against fixation member 18, as shown in dashed line. Referring to FIGS. 13A and 13B, knot 230 includes three crossing points, labeled, 230a, 230b, and 230c. When under tension, T, knot 230 tends to tighten upon itself, rather than slide in the direction of arrow 240 making it difficult to advance knot 230 along suture 10. To enable tension, T, to be applied to suture 10 at the same time knot 230 is advanced in the direction of arrow 240, a knot pusher 250 is used. Knot pusher 250 is configured to keep suture at crossing points 230a, 230b, and 230c from touching, such that knot 230 does not tighten upon itself under tension, T. This permits knot 230 to slide along the tensioned suture when knot pusher 250 is advanced in the direction of arrow 240.

Knot pusher 250 has a cylindrical body 215 and an end post 254. Body 215 defines a first groove 254 and a second groove 256 on one surface, and a third groove 258 that is an extension of groove 256 on an opposite surface. Grooves 254 and 256 form and X pattern, and grooves 256 and 258 define a loop 260 extending around body 215. The three grooves differ in depth, with groove 256 being the shallowest and groove 258 being the deepest. Thus, when suture 10 is formed into an overhand knot and positioned within grooves 254, 256, and 258, the suture at crossing points 230a, 230b, and 230c does not touch. Once knot 230 is advanced against fixation member 18, knot pusher 250 is removed by pulling retrograde on the knot pusher. To aid in removal of knot pusher 250, a tube (not shown) can be advanced over knot pusher 250 between the knot pusher and the suture. As the tube is advanced past suture crossing point 230a, the suture is stripped from knot pusher 250.

Figure 14:
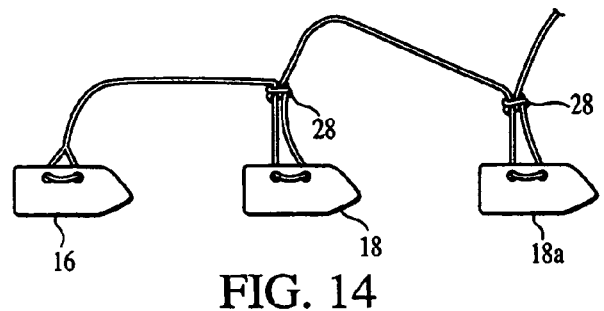
FIG. 14 is an illustration of an alternative embodiment of a closure device.

Referring to FIG. 14, one or more additional fixation members 18a with a slip knot 28 formed in suture 10 can be added to device 8. In use, fixation members 16 and 18 are implanted as described above, with suture 10 being tightened to secure fixation members 16 and 18 in place. Additional fixation member 18a is then implanted and suture 10 tightened to secure fixation member 18a in place. To accommodate additional fixation members, slot 110 in needle 100 of delivery device 99 is extended. To permit access to fixation member 18 by push rod 170, additional fixation members 18a preferably include a through bore (not shown) for passage therethrough by push rod 170. Push rod 170 preferably is biased off angle such that when push rod 170 is pulled out of the passage in fixation member 18a, the push rod is no longer aligned with the passage. Subsequent advancement of push rod 170 then engages an end face of fixation member 18a to push the fixation member toward the tip of the needle 100, rather than back through the passage. Slider 190 is preferably spring loaded such that after fixation member 18 is pushed out of needle 100, push rod 170 springs back to engage the next fixation member 18a.

Figure 14A:
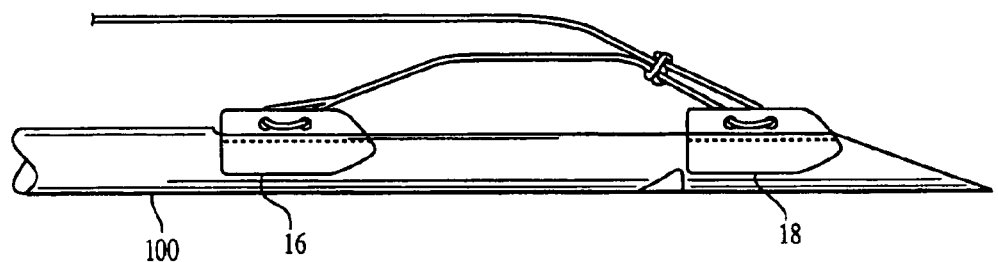
FIG. 14A shows an alternative arrangement of the closure device and delivery device of FIG. 14.
Figure 14B:
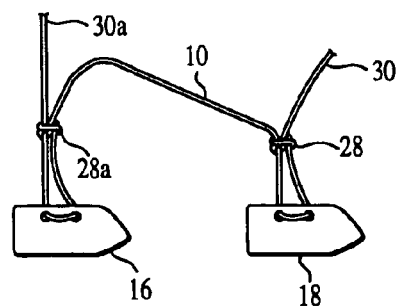
FIG. 14B is an illustration of an alternative embodiment of a closure device.

Referring to FIG. 14A, the positions of fixation member 16 and 18 in needle 100 can be swapped, with fixation member 18 located in distal region 112 such that fixation member 18 is implanted in the tissue prior to implantation of fixation member 16. Referring to FIG. 14B, rather than suture 10 being fixed to fixation member 16, here suture 10 is attached to fixation member 16 the same as the attachment to fixation member 18, such that a second slip knot 28a is formed and a second free end 30a of suture extends from fixation member 16. To secure fixation members 16 and 18, both ends 30 and 30a of suture 10 are pulled.

Figure 15:
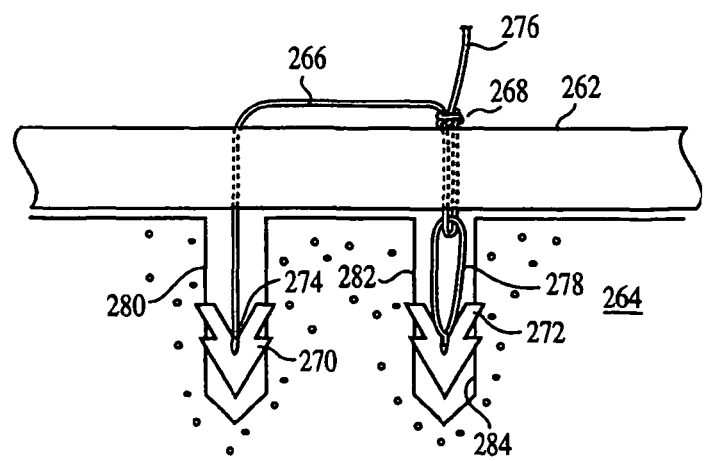
FIG. 15 is an illustration of an alternative embodiment of a closure device for use in attaching soft tissue to bone.

Referring to FIG. 15, in an application for securing soft tissue 262 to bone 264, a suture 266 is attached to fixation members in the form of a first anchor member 270 and a second anchor member 272. Members 270, 272 are, for example, TAG WEDGE bone anchors available from Smith & Nephew, Inc. Endoscopy Division, Andover, Mass. Other bone anchors known in the art can be employed. Suture 266 has a first end 274 fixed to anchor member 270, a second free end 276, and a slip knot 268, formed as described above for slip knot 28. Suture 266 preferably passes through a separate suture loop 278, rather than through 272 itself. Suture loop 278 acts as a good pulley allowing suture 266 to slide relative to suture loop 278.

In use, the user forms bone holes 280, 282 in bone 264. The user then implants anchor member 270 in bone hole 280, with suture 266 already threaded as shown, followed by implanting anchor member 272 in bone hole 282. The user then pulls on free end 276 of suture 266, which brings soft tissue 262 against bone 264. Slip knot 268 limits loosening of suture 266. By using suture loop 278, suture 266 is not located within bone hole 282 in use thus limiting the possibility of trapping suture 266 against wall 284 of bone hole 282. If suture 266 were trapped in bone hole 282, pulling free end 276 of suture 266 would not result in shortening the length of suture between anchors 270, 272, which acts to secure soft tissue 262 against bone 264.

Figure 16A:
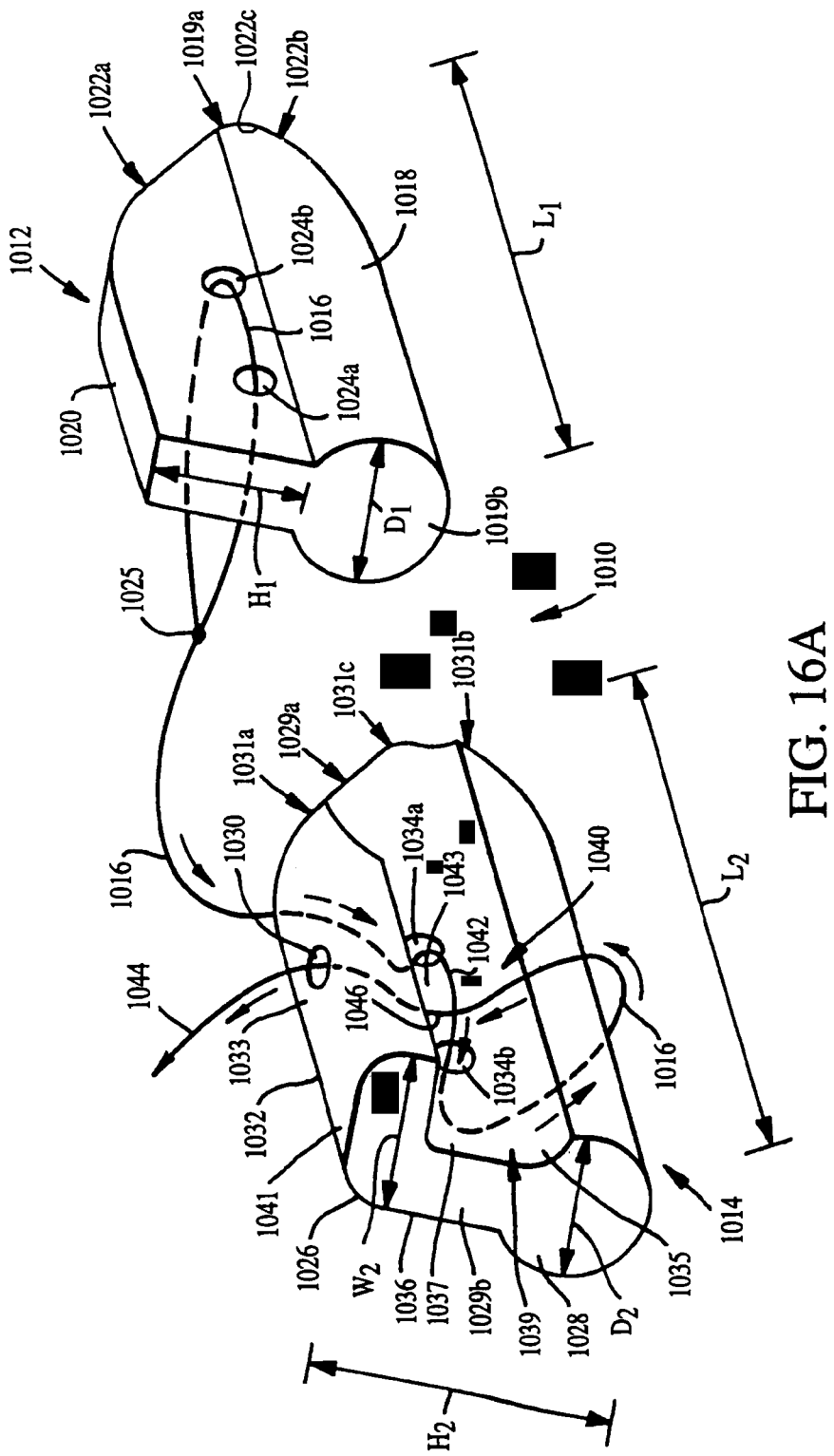
FIG. 16A is a perspective view of a wound closure device.
Figure 16B:
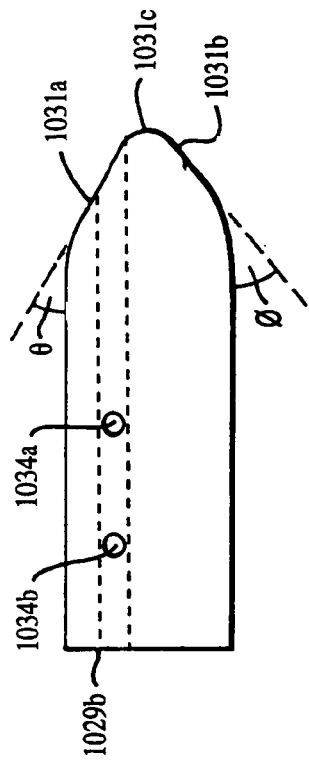
FIG. 16B is a side view of a first suture anchor of the wound closure device of FIG. 16A.
Figure 16C:
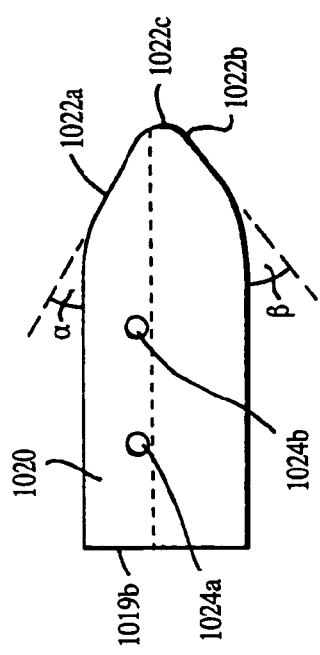
FIG. 16C is a side view of a second suture anchor of the device of FIG. 16A.

Referring to FIGS. 16A-16C, a wound closure device 1010 includes a first suture anchor 1012, a second suture anchor 1014, and a flexible member, e.g., suture 1016 that connects anchor 1012 to anchor 1014. The suture is tied to the first anchor with a conventional knot, but movably attached to the second anchor, allowing a surgeon to shorten the length of suture between the anchors, and thereby close a wound. First anchor 1012 has a generally solid cylindrical body 1018 extending axially from a distal surface 1019a to a flat proximal surface 1019b. To facilitate passage of first anchor 1012 into tissue, both an upper portion 1022a and a lower portion 1022b of surface 1019a are beveled relative to the axis of cylindrical body 1018, forming a rounded distal tip 1022c. Upper portion 1022a is beveled at an angle $\alpha$ relative to the axis of cylindrical body 1018, and lower portion 1022b is beveled at an angle $\beta$ relative to the axis.

Attached to cylindrical body 1018 is a fin-shaped projection 1020 that extends from upper portion 1022a of distal surface 1019a to proximal surface 1019b. Fin 1020 defines two horizontally transverse holes, 1024a and 1024b. Suture 1016 is attached to first anchor 1012 by passing the suture through hole 1024a in a first direction (e.g., out of the page in FIG. 16A), through hole 1024b in a second direction (e.g., into the page in FIG. 16A), and then forming a conventional knot 1025 near fin 1020. Conventional knot 1025 rigidly fixes suture 1016 to the first anchor.

Second anchor 1014 has a distal surface 1029a, a proximal surface 1029b, and a generally cylindrical body 1028 extending axially from surface 1029a to surface 1029b. Attached to body 1028 is an appendage 1026. Appendage 1026 is generally L-shaped in cross-section, and extends along an axial length of body 1028, from surface 1029a to surface 1029b.

Distal surface 1029a of anchor 1014 is beveled in a manner similar to anchor 1012: an upper portion 1031a of surface 1029a forms an angle $\theta$ relative to an axis of body 1028, and a lower portion 1031b of surface 1029a forms an angle $\phi$ relative to the body's axis, forming a rounded distal tip 1031c. Proximal surface 1029b of anchor 1014 is flat.

The L-shape of appendage 1026 is formed by two perpendicular sections: a stem 1036 attached to cylindrical body 1028 along an axial length of the body, and a base 1032 attached to the stem. Base 1032 defines a vertically transverse hole 1030, and stem 1036 defines two horizontally transverse holes 1034a and 1034b. Holes 1034a and 1034b are perpendicular to hole 1030, but all three holes pass through anchor 1014 in a direction generally parallel to sides 1029a and 1029b.

Each of the three holes 1034a, 1034b, and 1030 connect the exterior of anchor 1014 to an interior, partially enclosed, protected region 1039. Region 1039 is defined by base 1032, an interior surface 1037 of stem 1036, and a concave groove 1035 within cylindrical body 1028. Groove 1035 extends axially across body 1028, along the line where interior surface 1037 connects to body 1028.

Suture 1016 is movably attached to second anchor 1014 with a one-way knot 1040. One-way knot 1040 includes a first portion of suture 1016 that forms a loop 1042, and a second portion of suture that passes around body 1028 and through the loop. Loop 1042 is formed within the protective region 1039 defined by groove 1035, surface 1037, and base 1032. Region 1039 acts to separate loop 1042 from tissue when device 1010 is implanted within tissue, preventing the tissue from interfering with the sliding action of one-way knot 1040.

To form one-way knot 1040, suture 1016 is first passed from an exterior of anchor 1014, through hole 1034a into region 1039, and then back out hole 1034b to the exterior, forming loop 1042 within region 1039. The suture is then passed over the rounded, exterior surface 1041 of cylindrical body 1028, back into region 1039, through loop 1042, and then to the exterior through hole 1030. Suture 1016 terminates at a free end 1044.

One-way knot 1040 allows the length of suture between first anchor 1012 and second anchor 1014 to be shortened, but not lengthened. A surgeon can shorten the length of suture between the anchors by pulling on free end 1044, which draws additional suture in the direction of the arrows in FIG. 16A, through holes 1030, 1034b, and 1034a, thereby reducing the length of suture between anchors 1012 and 1014. If, however, the surgeon attempts to lengthen the distance between the anchors, e.g., by pulling first anchor 1012 away from second anchor 1014 (i.e., pulling suture 1016 in the opposite direction of the arrows), then loop 1042 squeezes portion 1046 of suture 1016 against an interior compression surface 1043 of stem 1036, preventing further lengthening of the distance between the anchors.

Figure 16D:
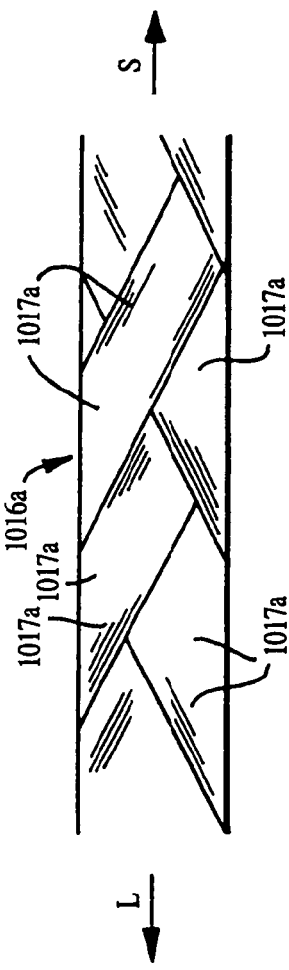
FIG. 16D is an enlarged view of a braided suture.

If suture 1016 is a braided suture, as opposed to a smooth suture, then suture 1016 should be threaded through second anchor 1014 in a particular direction. Referring to FIG. 16D, a braided suture 1016a is formed from numerous threads 1017a braided from left to right in FIG. 16D. Braided suture 1016a slides more easily if it is pulled in the direction of braiding (i.e., in the direction of arrow S in FIG. 16D) than if it is pulled against the braiding (in the direction of arrow L). Thus, if suture 1016 is a braided suture, then suture 1016 should be threaded through second anchor 1014 in the direction of braiding. If threaded in the direction of braiding, the suture will slide more easily in the direction of the arrows in FIG. 16A, and less easily in the direction opposing the arrows.

The cylindrical portions of anchors 1012 and 1014 are sized and shaped to fit within a hollow bore of a needle (described below), facilitating arthroscopic implantation of device 1010. For example, cylindrical body 1018 has a diameter $D_1$ of about 0.04 inches, and cylindrical body 1028 has a diameter $D_2$ approximately equal to diameter $D_1$. Fin-shaped projection 1020 and L-shaped appendage 1026, however, are configured to protrude through a longitudinal slit in the needle. Delivery of device 1010 using a hollow needle is described below, with reference to FIGS. 20A-20D and 21A-21D.

First anchor 1012 has an overall axial length $L_1$ of, e.g., about 0.19 inches, and fin 1020 has a height $H_1$ of, e.g., about 0.03 inches. Second anchor 1014 has an overall axial length $L_2$ of, e.g., about 0.22 inches, a width $W_2$ of, e.g., about 0.06 inches, and a height $H_2$ of, e.g., about 0.07 inches. Angle $\alpha$ is, e.g., about 30 degrees, angle $\beta$ is, e.g., about 40 degrees, angle $\theta$ is, e.g., about 30 degrees, and angle $\phi$ is, e.g., about 40 degrees.

Anchors 1012 and 1014 are made from rigid, biocompatible materials, such as polyethylene, an acetal, or polypropylene. Alternatively, the anchors can be made from resiliently deformable materials, as described in Hayhurst, supra, or from bioabsorbable materials. Anchors 1012 and 1014 are preferably unitary, injection molded pieces, but can also be manufactured by other methods.

Figure 17:
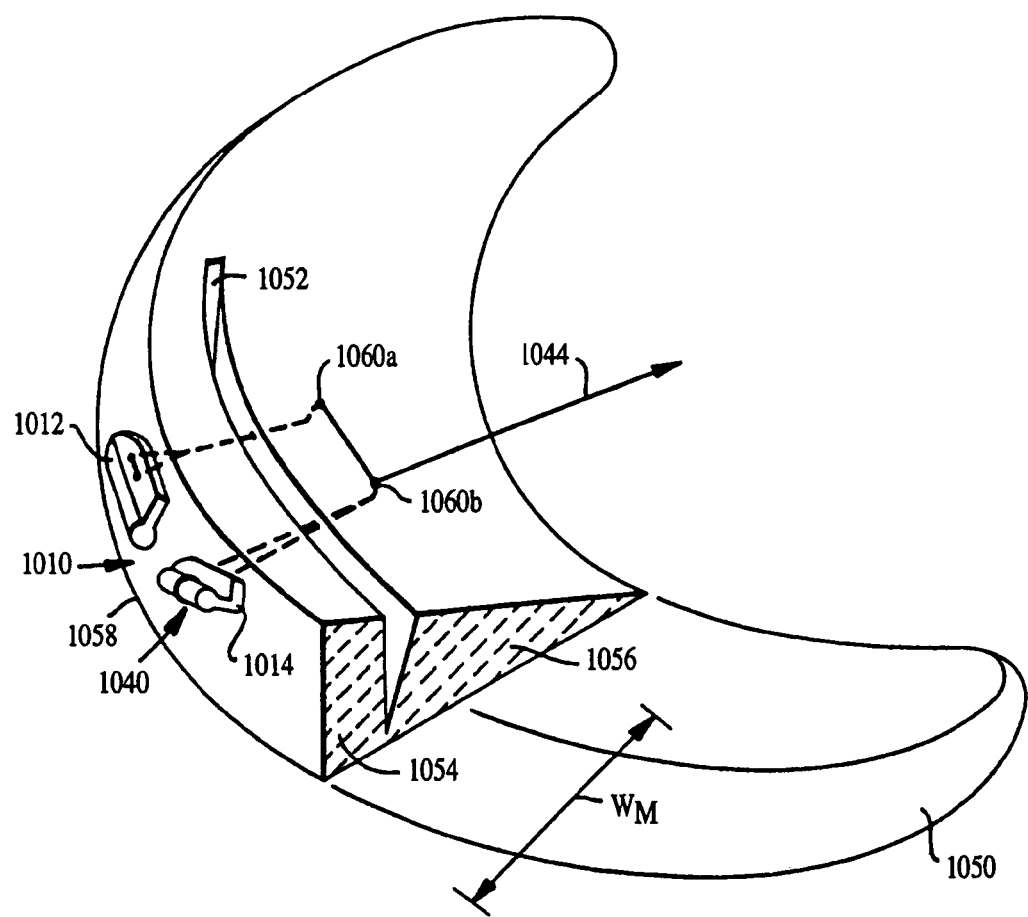
FIG. 17 is a perspective, cut-away view of the wound closure device of FIG. 17A implanted within a meniscus.

FIG. 17 illustrates the use of wound closure device 1010 to repair a torn meniscus 1050. Meniscus 1050 is a C-shaped, rubbery, shock-absorbing structure located between the tibia and femur inside the knee. Meniscus 1050 has a tear 1015 that unnaturally separates distal meniscal tissue 1054 from proximal tissue 1056. A width $W_M$ of meniscus 1050, as measured from points 1060a and 1060b to an exterior surface 1058 of the meniscus is, e.g., about 0.25 inches.

When device 1010 is implanted within meniscus 1050, both anchors 1012 and 1014 abut surface 1058, separated by a distance of, e.g., about 1 cm. Suture 1016 passes from first anchor 1012, into distal tissue 1054, across tear 1015, and emerges from proximal tissue 1056 at point 1060a. Suture 1016 then passes again into proximal tissue 1056 at point 1060b, again traverses tear 1015, and emerges out surface 1058, where it attaches to second anchor 1014 via one-way knot 1040. From second anchor 1040, suture 1016 passes again into distal tissue 1054, traverses tear 1015, and emerges from proximal tissue 1056 at or near point 1060b. Free end 1044 of suture 1016 emerges from proximal tissue 1056.

Figure 18A:
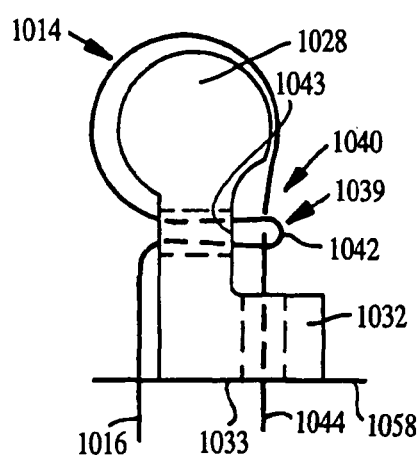
FIGS. 18A and 18B are sectional views of the second suture anchor and one-way knot of the wound closure device of FIG. 16A.
Figure 18B:
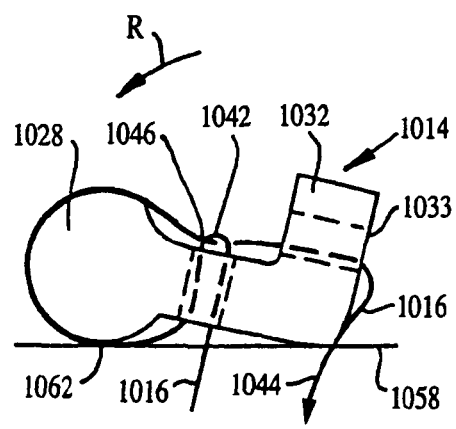

Referring to FIGS. 17, 18A, and 18B, once device 1010 is implanted, a surgeon can close tear 1015 by pulling on free end 1044 of suture 1016. When the surgeon pulls on free end 1044, four separate movements occur in succession. First, friction between suture 1016 and body 1028 rotates second anchor 1014 until a lower surface 1033 of base 1032 is flush against meniscal surface 1058, as shown in FIG. 18A. Second, tension in suture 1016 pulls the center of fin 1020 towards surface 1058, causing first anchor 1012 to align against surface 1058 transversely to the portion of suture 1016 that exits anchor 1012, with both fin 1020 and the axial length of body 1018 pressing against meniscal surface 1058. Third, continued pulling on free end 1044 draws additional suture through holes 1030, 1034b, and 1034a, via knot 1040, in the direction of the arrows of FIG. 16A, lengthening free end 1044 and shortening the length of suture between anchors 1012 and 1014. Shortening the length of suture between anchors 1012 and 1014 increases the tension in suture 1016 between the anchors, which pulls distal tissue 1054 and proximal tissue 1056 together, closing tear 1015. Since loop 1042 remains within protected region 1039 as the surgeon pulls on free end 1044, base 1032 separates loop 1042 from tissue, and suture 1016 does not become wedged between tissue and anchor 1014 when the surgeon pulls on the suture's free end. Once tear 1015 has been closed, one-way knot 1040 prevents the two anchors from pulling apart, and prevents the tear from re-opening.

The final successive movement occurs when the surgeon releases free end 1044, after closing tear 1015. When the surgeon releases the free end, the tension in suture 1016 between the two anchors pulls body 1028 of anchor 1014 away from free end 1044, causing second anchor 1014 to rotate in the direction of arrow R (FIG. 18B), until body 1028 abuts meniscal surface 1058, trapping a portion 1062 of suture 1016 between body 1028 and surface 1058. (For clarity, suture 1016 is shown spaced slightly from body 1028 and stem 1036 in FIG. 18B. In actuality, suture 1016 is flush against the surfaces of anchor 1014 after suture 1016 is tensioned by the surgeon.)

When second anchor 1014 is in its final position, shown in FIG. 18B, suture 1016 is locked in place. The length of suture between anchors 1012 and 1014 cannot be increased, because loop 1042 of one-way knot 1040 presses portion 1046 of the suture against surface 1043 of stem 1036. In addition, the length of suture between the anchors resists being further shortened, since portion 1062 of suture 1016 is wedged between body 1028 and surface 1058 of the meniscus.

Figure 19:
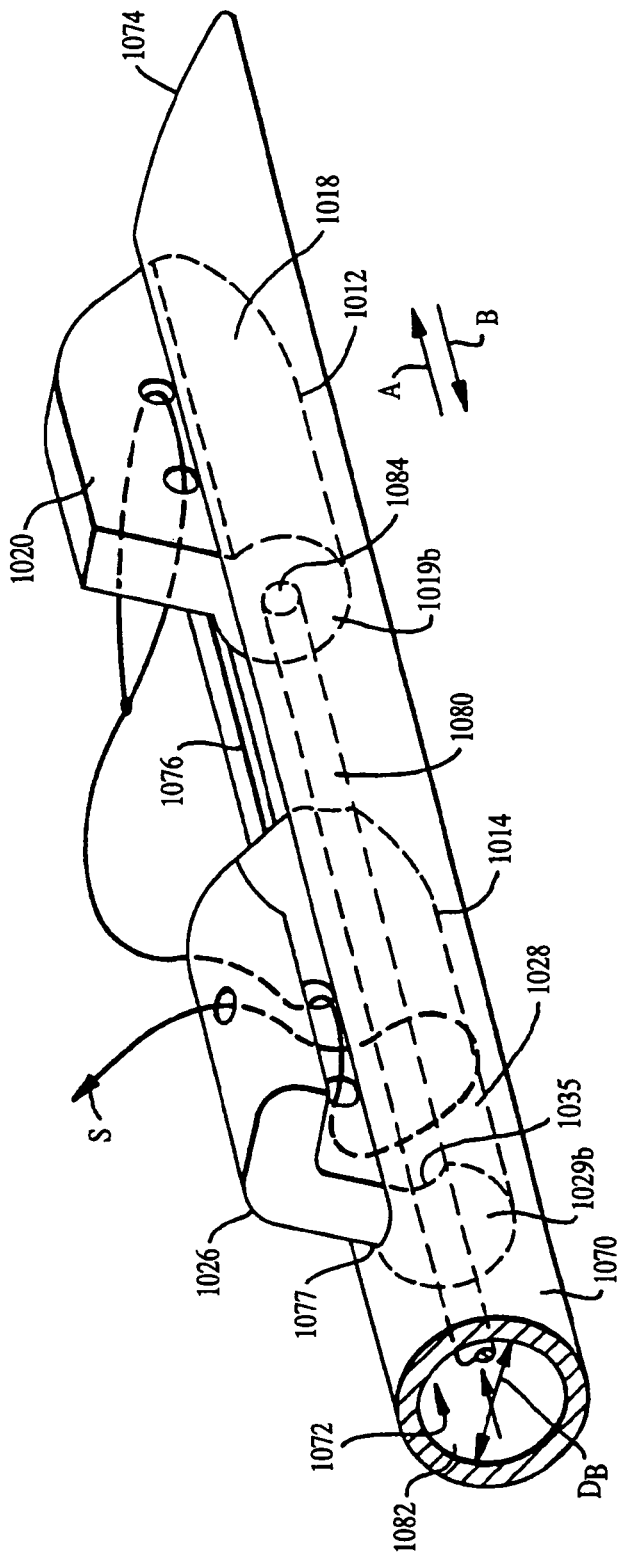
FIG. 19 is a perspective view of a hollow needle, with the wound closure device of FIG. 16A disposed within a bore of the needle.

Wound closure device 1010 is preferably deployed within meniscus 1050 arthroscopically, using a hollow needle 1070. Referring to FIG. 19, hollow needle 1070 defines a bore 1072 and an open distal tip 1074. The diameter $D_B$ of bore 1072 is slightly larger than diameter $D_1$ of body 1018 of first anchor 1012, and diameter $D_2$ of body 1028 of second anchor 1014, allowing body 1018 and body 1028 to fit slidably within the bore. Needle 1070 also includes a longitudinal slit 1076 through a wall of the needle. Slit 1076 extends proximally from open tip 1074, and communicates with bore 1072. Slit 1076 is sized and shaped to allow fin 1020 of first anchor 1012 and L-shaped appendage 1026 of second anchor 1014 to protrude from needle 1070.

Needle 1070 also includes a plunger 1080. Plunger 1080 enters bore 1072 through a proximal opening 1082 in needle 1070, and extends to proximal surface 1019b of first anchor 1012. Plunger 1080 passes by second anchor 1014 by sliding along groove 1035. When plunger 1080 is positioned as shown in FIG. 19, sliding plunger 1080 in the direction of arrow A pushes first anchor 1012 distally, but does not move second anchor 1014.

Prior to surgery, suture 1016 is attached to anchors 1012 and 1014, in the manner described above with reference to FIG. 16A. The two anchors 1012 and 1014 are then loaded into bore 1072 of needle 1070. Second anchor 1014 is loaded first, by inserting cylindrical head 1028 into bore 1072, through open tip 1074, such that appendage 1026 protrudes through slit 1076. Second anchor 1014 is pushed proximally into slit 1076, until stem 1036 abuts a proximal surface 1077 of the slit. Next, first anchor 1012 is loaded into the distal most position in needle 1070 by inserting cylindrical body 1018 through tip 1074, into bore 1072, such that fin 1020 protrudes through slit 1076. Both anchors 1012 and 1014 are loaded with their respective beveled distal surfaces 1019a and 1029a facing open distal tip 1074.

After the anchors have been loaded, plunger 1080 is inserted into bore 1072 through proximal opening 1082. Plunger 1080 is slid past second anchor 1014 along groove 1035, until a tip 1084 of the plunger abuts proximal surface 1019b of first anchor 1012.

Attachment of suture 1016 to anchors 1012 and 1014 and loading of the anchors and plunger into needle 1070 can be performed at the time of manufacture, i.e., pre-loaded, or immediately prior to surgery.

During surgery (or prior to surgery), the surgeon first pushes plunger 1080 in the direction of arrow A to separate anchors 1012 and 1014 within bore 1072. The surgeon pushes the plunger until the anchors are separated by at least a distance L, as shown in FIG. 19, where L is greater than width $W_M$ of meniscus 1050. Distance L is, e.g., about 0.35 inches.

Referring to FIGS. 17 and 20A-20D (not to scale), the surgeon next pushes needle 1070 through meniscus 1050, in the direction of arrow A, until fin 1020 of first anchor 1012 passes entirely through exterior surface 1058 of the meniscus. As the surgeon pushes needle 1070 through the tissue, he or she holds plunger 1080 steady, to prevent anchor 1012 from sliding in the direction of arrow B as the needle is pushed through the meniscal tissue. Since the separation distance L is greater than the width $W_M$ of meniscus 1050, second anchor 1014 does not enter the meniscus at this point in the procedure.

Figure 20A:
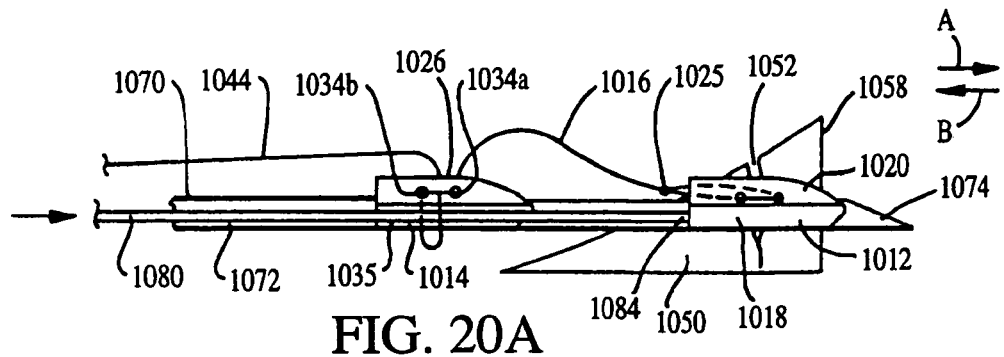
FIGS. 20A-20D are schematics illustrating deployment of the wound closure device of FIG. 16A into a meniscus using a plunger.
Figure 20B:
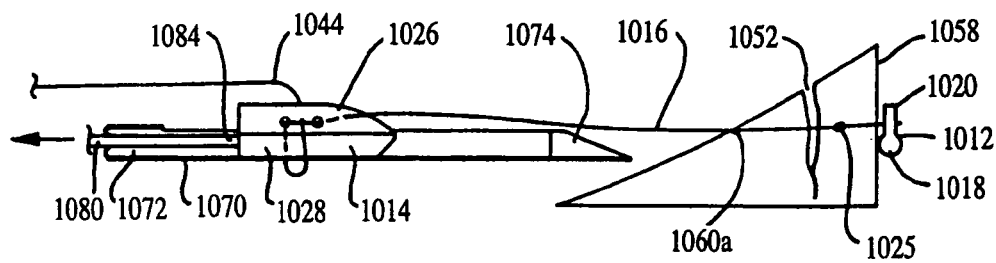
Figure 20C:
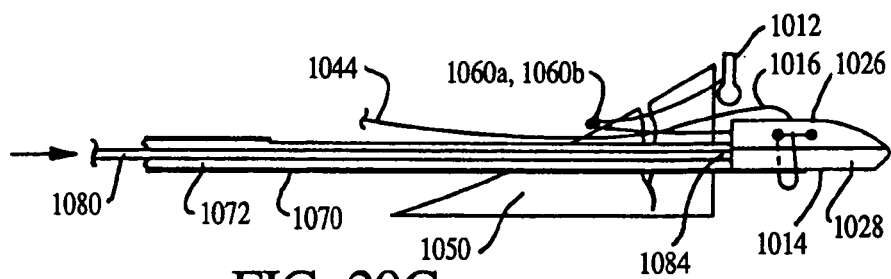

The surgeon next forces first anchor 1012 out of needle 1070 through tip 1074 by pushing plunger 1080 in the direction of arrow A, and then seats anchor 1012 against surface 1058 of the meniscus by pulling on free end 1044 of suture 1016. Once anchor 1012 has been seated, needle 1070 is pulled in the direction of arrow B, back through meniscus 1050, across tear 1015, and out the hole at point 1060a (FIG. 20B).

Figure 20D:
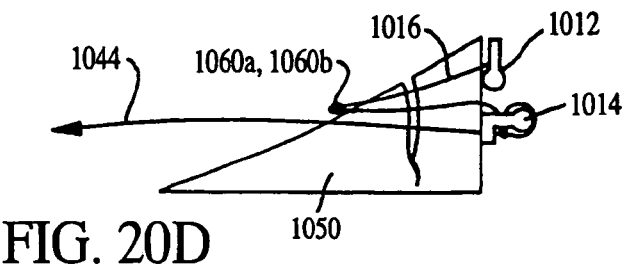

The surgeon then reinserts needle 1070 into meniscus 1050 at point 1060b, and again passes the needle through the meniscus in the direction of arrow A, across tear 1015, until tip 1074 passes through surface 1058. To eject second anchor 1014, the surgeon withdraws plunger 1080 in the direction of arrow B until tip 1084 of the plunger is proximal to surface 1029b of anchor 1014. The surgeon then maneuvers plunger 1080 until tip 1084 contacts surface 1029b, and then pushes the plunger in the direction of arrow A, forcing second anchor 1014 through tip 1074. Plunger 1080 and needle 1070 are then fully withdrawn in the direction of arrow B, leaving both anchors 1012 and 1014 resting against surface 1058, as shown in FIG. 20D. The surgeon can then tension suture 1016, positioning the anchors against surface 1058 and closing tear 1015, by pulling on free end 1044, as described above with reference to FIG. 17.

Alternative deployment methods are possible. For example, device 1010 can be extracted from needle 1070 by engaging fin 1020 with surface 1058, rather than by using a plunger 1080. Referring to FIG. 21A-21D (not to scale), in this embodiment, plunger 1080 is not passed through groove 1035 to first anchor 1012. Instead, tip 1084 of plunger 1080 always remains proximal to anchor 1014.

When the two anchors are loaded into bore 1072 of needle 1070, a spacer 1086 is placed between the anchors. Spacer 1086 is a simple cylindrical bar, preferably made from a material that degrades quickly in the body, such as salt. Spacer 1086 has a longitudinal length $L_S$ greater than width $W_M$ of meniscus 1050. Length $L_S$ is, e.g., about 0.35 inches.

Figure 21A:
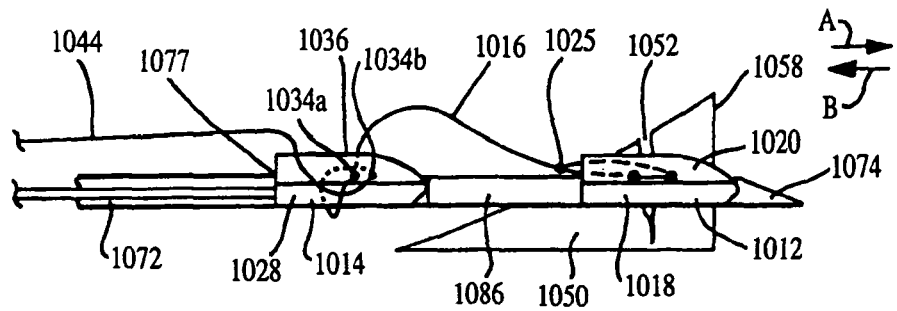
FIGS. 21A-21D are schematics illustrating deployment of the wound closure device of FIG. 16A into a meniscus using a plunger and a spacer.

During surgery, the surgeon first pushes needle 1070 through meniscus 1050, in the direction of arrow A, until fin 1020 passes entirely through exterior surface 1058 of the meniscus (FIG. 21A). As the surgeon pushes needle 1070 through the tissue, surface 1077 of slit 1076 engages stem 1036 of anchor 1014, preventing the two anchors and the spacer from sliding in the direction of arrow B within bore 1072. (In addition, the surgeon can hold plunger 1080 steady to prevent the two anchors from sliding in the direction of arrow B.)

Figure 21B:
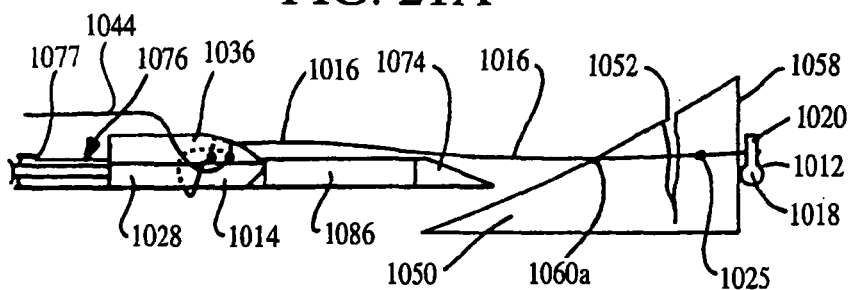

The surgeon next pulls the needle in the direction of arrow B, back through meniscus 1050, across tear 1015, and out the hole at point 1060a (FIG. 21B). As the surgeon withdraws the needle, fin 1020 engages surface 1058, and first anchor 1012 is pulled out of needle 1070, through tip 1074. As before, the surgeon then seats anchor 1012 against surface 1058 by pulling on free end 1044 of suture 1016. Since spacer 1086 is larger than width $W_M$ of meniscus 1050, the spacer prevents second anchor 1014 from entering meniscus 1050, and therefore prevents second anchor 1014 from also being pulled out of needle 1070 as needle 1070 is pulled in the direction of arrow B.

Figure 21C:
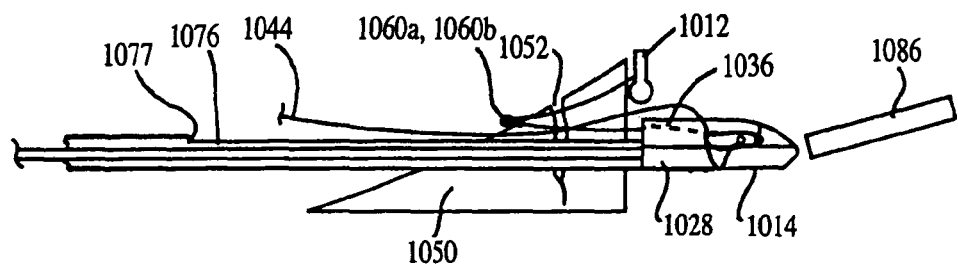
Figure 21D:
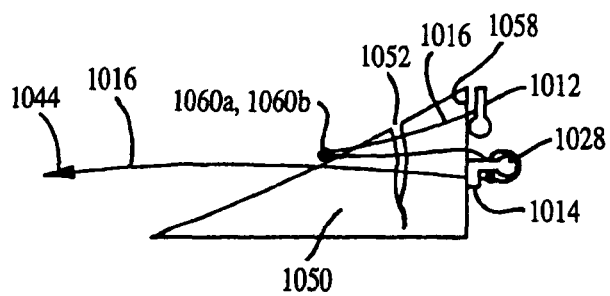

Next, the surgeon reinserts needle 1070 into meniscus 1050 at point 1060b, and again passes the needle through the meniscus in the direction of arrow A, across tear 1015, until tip 1074 passes through surface 1058. The surgeon then pushes plunger 1080 in the direction of arrow A, ejecting both spacer 1086 and second anchor 1014 out of needle 1070 through tip 1074 (FIG. 21C). The needle is then fully withdrawn from meniscus 1050, in the direction of arrow B, leaving both anchors 1012 and 1014 resting against surface 1058, as shown in FIG. 21D. The surgeon then pulls on free end 1044 to position the anchors and close the tear, as described above. Spacer 1086 can either be removed by the surgeon, or left within the body to degrade.

Figure 22A:
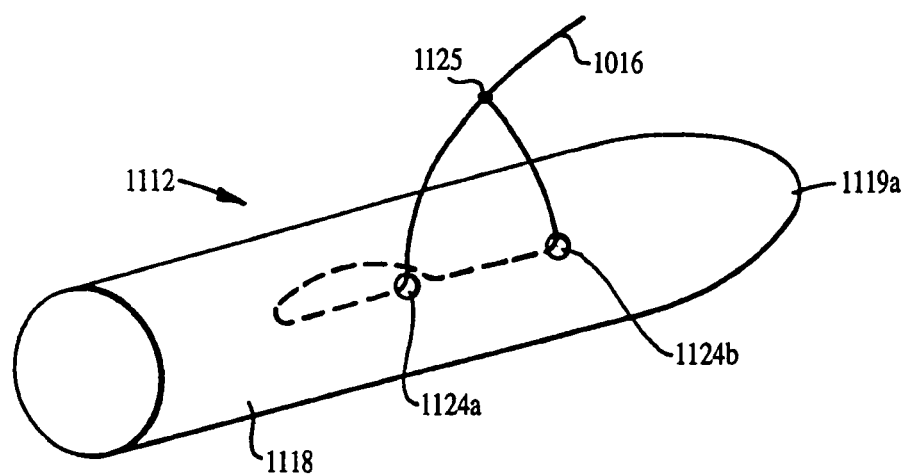
FIG. 22A is a perspective view of an alternative first anchor design for a wound closure device, used in reverse deployment of the device.
Figure 22B:
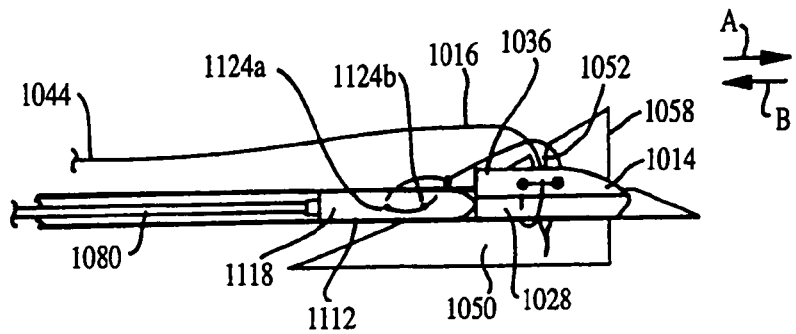
FIGS. 22B-22E are schematics illustrating reverse deployment of a wound closure device.

In another alternative deployment method, a modified wound closure device is deployed in meniscus 1050 in reverse, second anchor first. Referring to FIG. 22A, a modified wound closure device includes a first anchor 1112 that has a beveled face 1119a, but lacks a fin. Anchor 1112 has an axial, generally cylindrical body 1118 that defines two transverse holes 1124a and 1124b. Suture 1016 is attached to anchor 1112 by threading the suture through hole 1124a in a first direction, through hole 1124b in a second direction, and then tying a conventional knot 1125.

Referring to FIGS. 22B-22E (not to scale), in this reverse deployment embodiment, second anchor 1014 is positioned distally in bore 1072, with first anchor 1112 directly proximal. Tip 1084 of plunger 1080 resides immediately proximal to first anchor 1112 in bore 1072. In operation, the surgeon first pushes needle 1070 through meniscus 1050, in the direction of arrow A, until tip 1074 passes through surface 1058. The surgeon then pushes plunger 1080 in the direction of arrow A far enough to force second anchor 1014 through tip 1074, but not far enough to eject first anchor 1112.

Figure 22C:
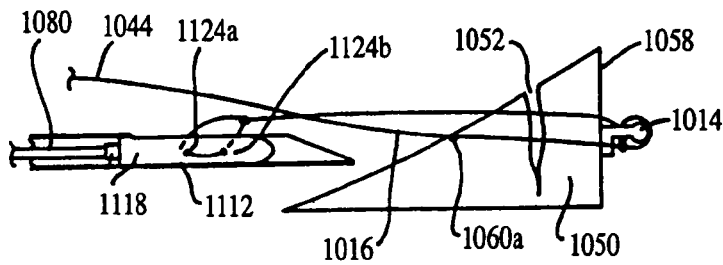
Figure 22D:
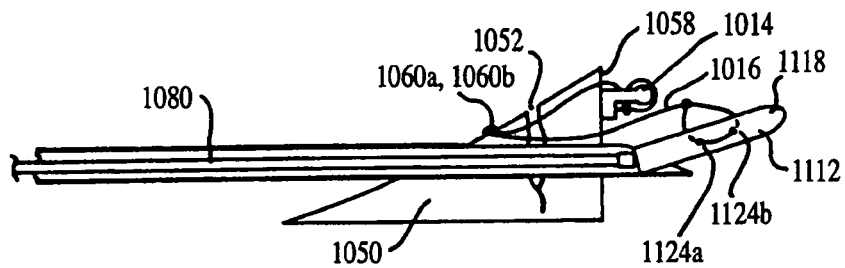
Figure 22E:
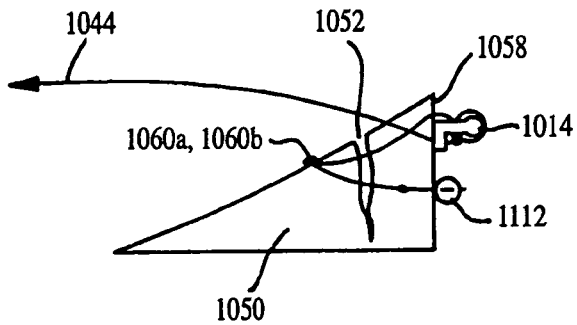

After anchor 1014 has been ejected, the surgeon pulls the needle in the direction of arrow B, back through meniscus 1050, across tear 1015, and out point 1060a (FIG. 22C). Since first anchor 1112 does not include a fin, it does not protrude through slit 1076, and does not engage tissue when the needle is pulled in the direction of arrow B. Next, the surgeon reinserts needle 1070 into the meniscus at point 1060b, and again passes the needle through meniscus 1050 in the direction of arrow A, across tear 1015, until tip 1074 passes through surface 1058. The surgeon then ejects first anchor 1112 by pushing plunger 1080 in the direction of arrow A, (FIG. 22D), and withdraws needle 1070 from meniscus 1050. The surgeon then positions the anchors and closes tear 1015 by pulling on free end 1044 (FIG. 22E), as described above.

Alternative configurations of second anchor 1014 and one-way knot 1040 are possible.

Figure 23A:
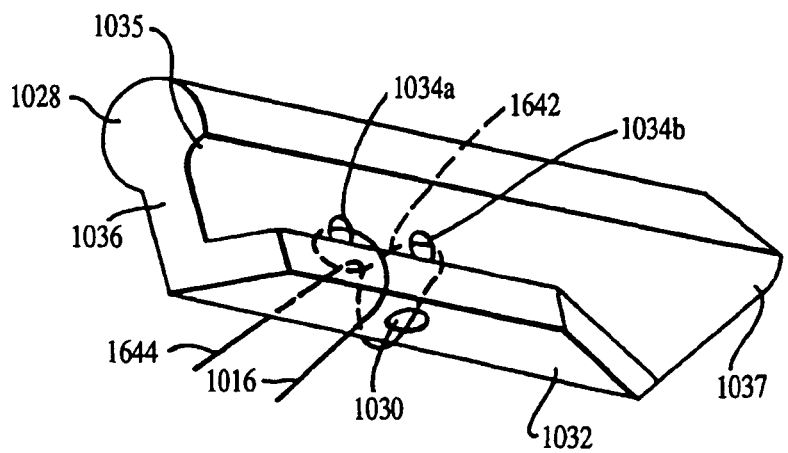
FIGS. 23A and 23B are perspective views of the second suture anchor of FIGS. 16A and 16C, showing an alternative one-way knot configuration for the anchor.
Figure 23B:
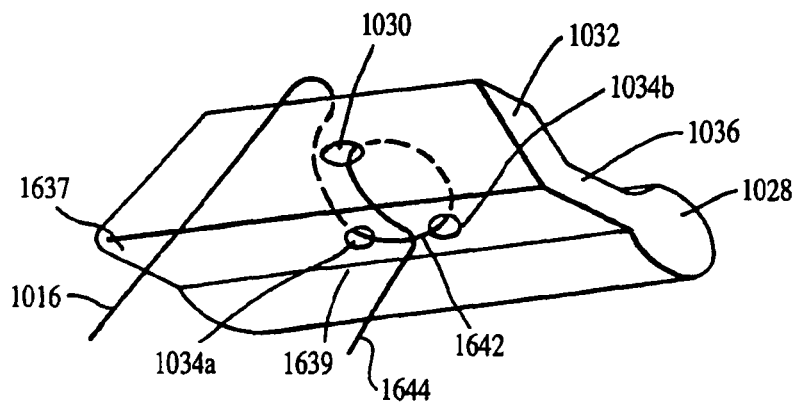

For example, referring first to FIGS. 23A and 23B, suture 1016 can be threaded through second anchor 1014 so that the loop is located against an exterior surface 1637 of stem 1036, rather than within region 1039. In this embodiment, suture 1016 is threaded through second anchor 1014 by first passing the suture around base 1032, into region 1039, and then out of region 1039 through hole 1034a. The suture then passes back into region 1039 through hole 1034b, forming a loop 1642 adjacent surface 1637. After forming the loop, the suture passes through hole 1030 to the exterior, and then through loop 1642, terminating at free end 1644.

When the surgeon pulls free end 1644 of suture 1016, the anchor rotates until surface 1637 faces surface 1058 of meniscus 1050 (FIGS. 17 and 18A-18B). Cylindrical body 1028 causes part of surface 1637 to remain elevated above surface 1058, creating a small gap 1639 that contains loop 1642. Loop 1642, therefore, does not become wedged between tissue and surface 1637 when the surgeon pulls free end 1644 to tension the suture.

Figure 24:
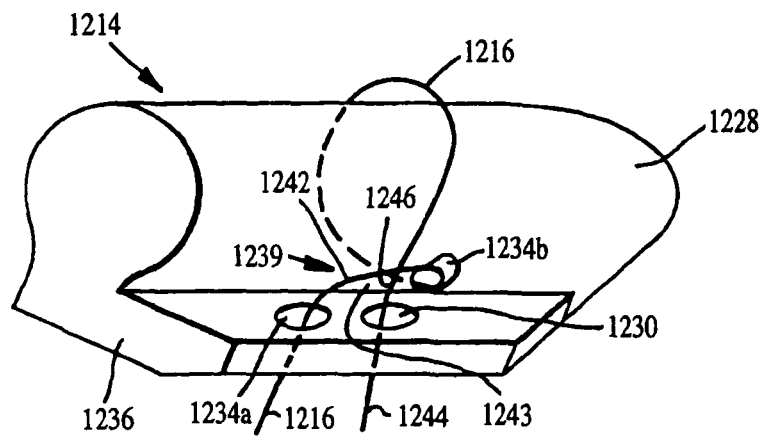
FIGS. 24-27 are sectional views of alternative configurations of the suture anchor and one-way knot of FIGS. 18A and 18B.

Referring to FIG. 24, second anchor 1214 has a structure similar to anchor 1014, except that anchor 1214 lacks a base 1032. Anchor 1214 includes a cylindrical body 1228 and a stem 1236 that define a wedge-shaped, partially enclosed region 1239 therebetween. Stem 1236 defines two holes, 1234a and 1230, and body 1228 defines one transverse hole 1234b. Holes 1234a and 1230 are generally parallel, and are both generally perpendicular to hole 1234b. A suture 1216 passes from a first anchor (not shown) through hole 1234a into region 1239, and then through hole 1234b to the exterior of the anchor, forming a loop 1242 within region 1239. The suture then wraps around body 1228 back into region 1239, through loop 1242, and out of region 1239 through hole 1230, terminating at free end 1244. Alternatively, suture 1216 can wrap around body 1228 two or more times before passing back into region 1239.

As in the previous embodiments, pulling on free end 1244 tensions suture 1216 and shortens the length of suture between the anchors. Pulling on suture 1216 in an opposite direction, however, causes loop 1242 to press a portion 1246 of the suture against a compression surface 1243. Since loop 1242 is located within protected region 1239, and is therefore spaced from the meniscal surface, loop 1242 does not become wedged between tissue and the anchor when the surgeon tensions suture 1216. Unlike the previous embodiments, however, anchor 1214 does not rotate after the surgeon tensions the suture and releases free end 1244.

Figure 25:
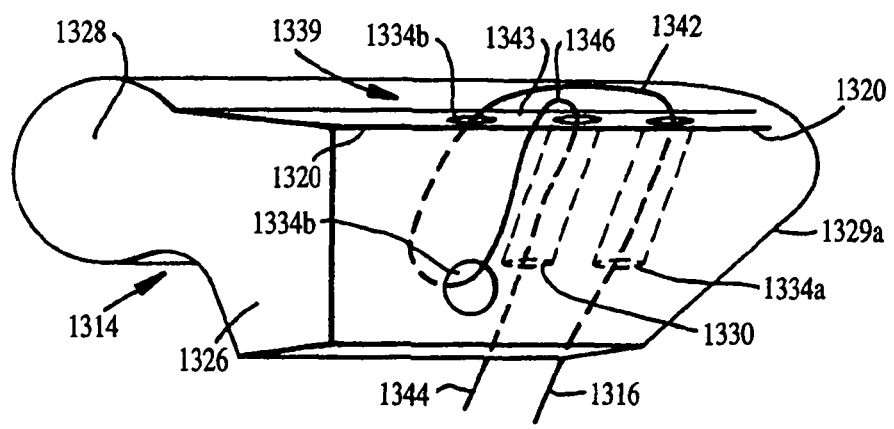

Referring to FIG. 25, second anchor 1314 includes a generally cylindrical body 1328 and an offset, generally rectangular appendage 1326. Appendage 1326 and body 1328 define a partially protected region 1339. As with anchor 1014, a front surface 1329a of anchor 1314 is beveled.

Appendage 1326 defines three holes, 1330, 1334a, and 1334b. Holes 1334a and 1330 are generally straight, while hole 1334b defines an arc through an inside of appendage 1326. A suture 1316 passes from a first anchor (not shown) through straight hole 1334a into region 1339. Suture 1316 then passes out of region 1339 through arc-shaped hole 1334b, forming a loop 1342 within region 1339. The suture then wraps around a corner 1320 of body 1326, passes through loop 1342, and through hole 1330, terminating at free end 1344. As with the embodiments of FIGS. 16, 22A-22B, and 23, pulling on free end 1344 shortens the length of suture between the anchors, but pulling on suture 1316 in an opposite direction causes loop 1342 to squeeze a portion 1346 of the suture against a compression surface 1343 of appendage 1326, preventing further movement. Like the embodiment of FIG. 23, anchor 1314 does not rotate after the suture is tensioned and released.

Figure 26:
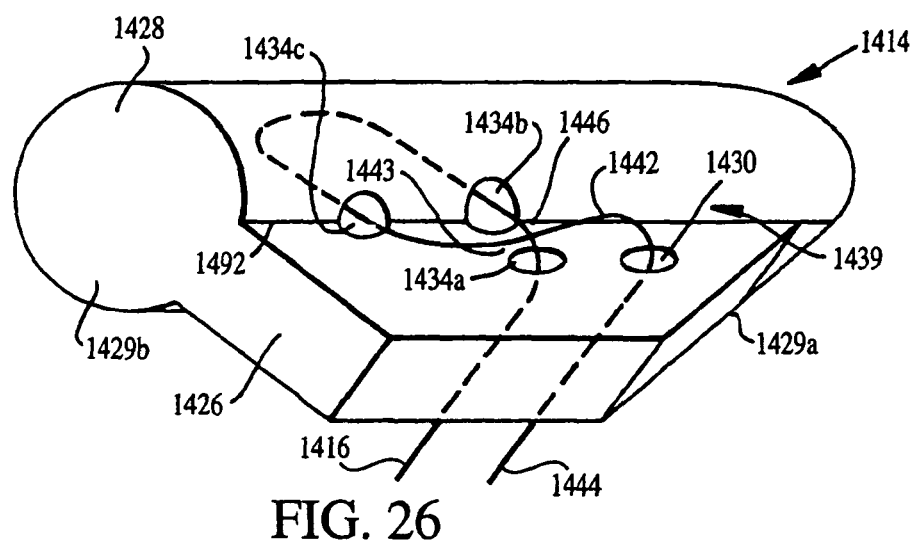

Referring to FIG. 26, second anchor 1414 includes a generally cylindrical body 1428 extending from a beveled distal surface 1429a to a flat proximal surface 1429b. A generally rectangular appendage 1426 also extends from surface 1429a to surface 1429b. Rectangular appendage 1426 is attached to body 1428 along the long side of the rectangle, and is centered along an axial length of body 1428. Body 1428 and appendage 1426 define a protected region 1439.

Appendage 1426 defines two holes, 1434a and 1430, and body 1428 defines two transverse holes, 1434b and 1434c. Hole 1434b is located entirely within body 1428, but hole 1434c is located at a juncture 1492 between body 1428 and appendage 1426. Holes 1434a and 1430 are generally parallel, and are both generally perpendicular to holes 1434b and 1434c.

A suture 1416 extends from a first anchor (not shown), through hole 1434a into region 1439, and then out of region 1439 through hole 1434b, forming a loop 1442 within region 1439. The suture then passes back into region 1439 through hole 1434c, through loop 1442, and out of region 1439 through hole 1430, terminating at free end 1444.

As with the other described second anchor embodiments, pulling on free end 1444 tensions suture 1416 and shortens the length of suture between the anchors, but pulling on suture 1416 in an opposite direction causes loop 1442 to squeeze a portion 1446 of the suture against a compression surface 1443 of appendage 1426, preventing further movement. Region 1439 is separated from the meniscal tissue by body 1428, preventing loop 1442 from wedging between anchor 1414 and tissue when the surgeon pulls on free end 1444. Anchor 1414 does not rotate after the surgeon tensions and releases the suture.

Figure 27:
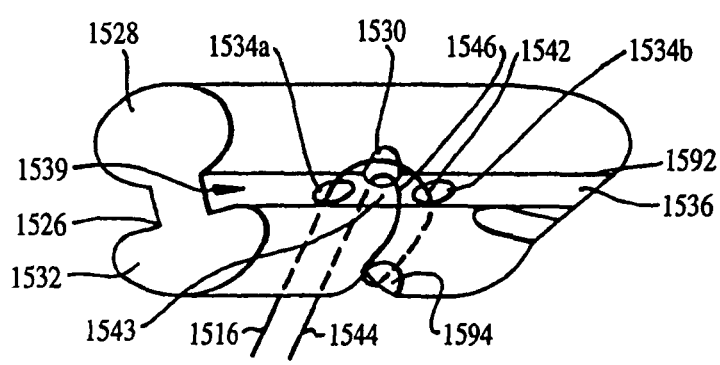

Referring to FIG. 27, second anchor 1514 includes a generally cylindrical body 1158 and an appendage 1156. Both body 1158 and appendage 1156 extend from a beveled distal surface 1159a to a flat proximal surface 1159b. Appendage 1156 includes a stem 1536 attached to body 1158, and a head 1532 attached to stem 1536. Stem 1536 is rectangular in cross-section and head 1532 is D-shaped in cross-section, giving appendage 1156 a mushroom-shaped cross-section. Stem 1536, head 1532, and body 1158 define a partially enclosed, protected region 1539.

Stem 1536 defines two transverse holes 1534a and 1534b, and body 1158 defines a single transverse hole 1530 located at a juncture 1592 between body 1158 and stem 1536. A suture 1516 passes from a first anchor (not shown), through hole 1534a into protected region 1539, and then out of region 1539 through hole 1534b, forming a loop 1542 within region 1539. Suture 1516 then passes around D-shaped head 1532 through a transverse groove 1594 in head 1532, back into region 1539, through loop 1542, and out hole 1530, terminating at free end 1544. As with the other described embodiments of the second anchor, pulling on free end 1544 shortens the distance between the two anchors, but pulling on suture 1516 in an opposite direction causes loop 1542 to squeeze a portion 1546 of the suture against a compression surface 1543 of stem 1536, preventing further movement. That loop 1542 is located within region 1539 prevents the loop from becoming wedged between the anchor and tissue when the surgeon pulls on free end 1544. Anchor 1514, like anchors 1214, 1314, and 1414, does not rotate after the surgeon tensions and releases the suture.

Referring to FIGS. 28A-28D and FIGS. 29-31, the second anchor can have a T shape or a crescent shape, and can be deployed at a surface of the meniscus or inter-body. Referring to FIGS. 28A and 28B, second anchor 1730 has a T-shape. The base 1732 of the T defines three through-holes, 1734a, 1734b, and 1734c, and the stem 1736 of the T is configured to penetrate meniscal tissue. Stem 1736 is offset from base 1732 so that the stem does not block hole 1734b. Referring to FIGS. 28C and 28D, second anchor 1814 has a flat, generally circular proximal surface 1836, and a rounded distal surface 1838, giving the anchor a generally hemispherical or "crescent" shape. (Alternatively, surface 1836 can be concave.) Anchor 1814 defines three through-holes, 1830, 1834a, and 1834b. The holes pass in an axial direction from the anchor's proximal circular surface 1836 to its distal rounded surface 1838.

Figure 29:
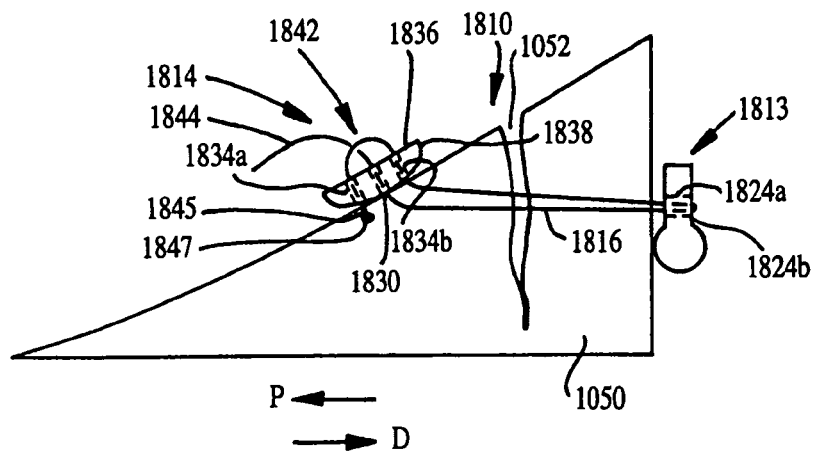
FIGS. 29-31 are sectional views showing deployment of wound closure devices that include the crescent-shaped suture anchor of FIG. 28C.

FIG. 29 illustrates deployment of a device 1810 that has a crescent-shaped second anchor 1814, and a "pulley" anchor 1813. Pulley anchor 1813 does not act as a dead-end for a suture, nor does it include a one-way knot. Instead, pulley anchor 1813 includes two through-holes, 1824a and 1824b. A suture 1816 passes through hole 1824a in a first direction, and then through hole 1824b in a second direction, such that suture 1816 can slide over pulley anchor 1813 in either direction. Pulley anchor 1813 can have the shape and structure of anchor 1012 (i.e., the holes are located on a fin), the simple cylindrical structure of anchor 1112 of FIG. 22A, or numerous other structures.

In operation, anchors 1813 and 1814 are deployed using, e.g., a hollow needle 1070, such that anchor 1814 is positioned on a proximal side of meniscus 1050, and anchor 1813 is deployed against distal surface 1058. When deployed, suture 1816 passes through hole 1834a of crescent-shaped anchor 1814 in a generally proximal direction (arrow P), from rounded surface 1838 to circular surface 1836, and then through hole 1834b in a generally distal direction (arrow D), forming a loop 1842. From loop 1842, the suture passes through meniscal tissue, through hole 1824*a* of pulley anchor 1813, through hole 1824*b* of anchor 1813, and back through meniscal tissue to the crescent shaped anchor. The suture then passes through loop 1842, terminating at free end 1844. The opposite end 1845 of suture 1816 includes a knob or a knot 1847 that prevents end 1845 from passing through hole 1834*a*. Thus, suture 1816 begins at anchor 1814, in addition to forming the one-way knot at anchor 1814.

Figure 30:
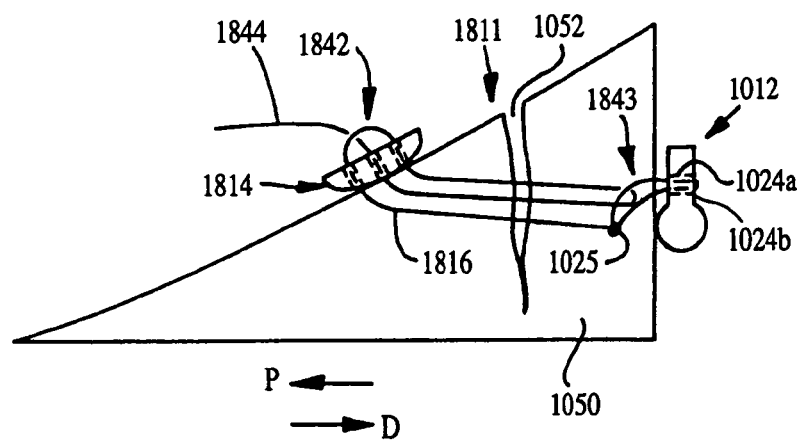

Referring to FIG. 30, rather than beginning at anchor 1814, the suture can be affixed to a first anchor 1012. In FIG. 30, a device 1811 includes a first anchor 1012 and crescent-shaped second anchor 1814. Suture 1816 passes through holes 1024*a* and 1024*b* of anchor 1012, forming a knot 1025 as shown in FIG. 16A. From knot 1025, suture 1816 passes through meniscal tissue and then through holes 1834*a* and 1834*b* of anchor 1814, forming loop 1842. From loop 1842, the suture passes back through meniscal tissue to first anchor 1012, and then through a fixed loop 1843 located between knot 1025 and first anchor 1012. The suture then passes back through meniscal tissue, through hole 1830 of anchor 1814, and through loop 1842, terminating at free end 1844.

When a surgeon pulls on free end 1844 in device 1811, the mechanical advantage is 3:1, since suture 1816 passes between the two anchors three times. By comparison, in device 1810, the mechanical advantage is 2:1.

Figure 31:
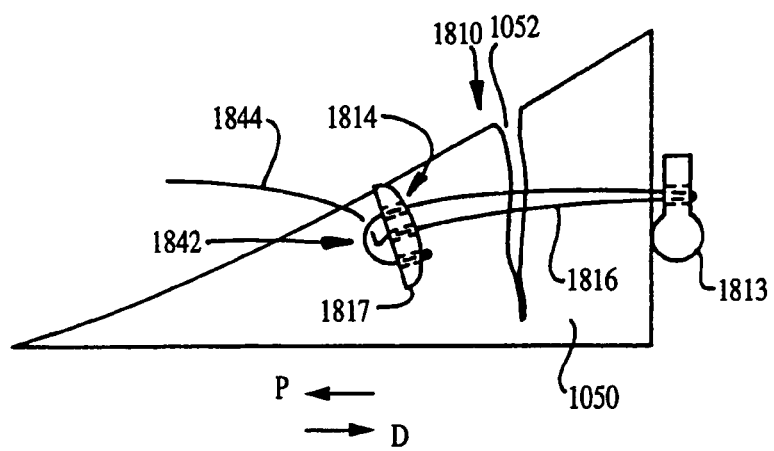

Referring to FIG. 31, the crescent shaped anchor 1814 of device 1810 can be deployed inter-body (i.e., embedded within meniscal tissue), rather than against a surface of the meniscus. In this deployment method, device 1810 is deployed in the manner described above with reference to FIG. 29, or using another deployment method. After positioning the anchors and tensioning free end 1844, however, the surgeon pushes anchor 1814 into the meniscal tissue, using, e.g., a needle. To facilitate pushing anchor 1814 into the tissue, a point 1817 of anchor 1814 can be sharp.

Other types of second anchors described herein, whether or not they include a sharp point, can also be positioned inter-body.

In each of the described embodiments of the second anchor, the one-way knot can be left "loose" until after both the first and second anchors are positioned against the meniscus. In such an embodiment, the suture would be very long, e.g., more than 12 cm long, such that the one-way knot includes considerable slack, and the loop portion of the knot is accessible to the surgeon's fingers. In this embodiment, the surgeon can position the first and second anchors against backside 1058 by pulling on both the free end and the loop itself. Once the anchors are satisfactorily positioned, the surgeon tightens the knot by pulling on the free end.

Figure 32:
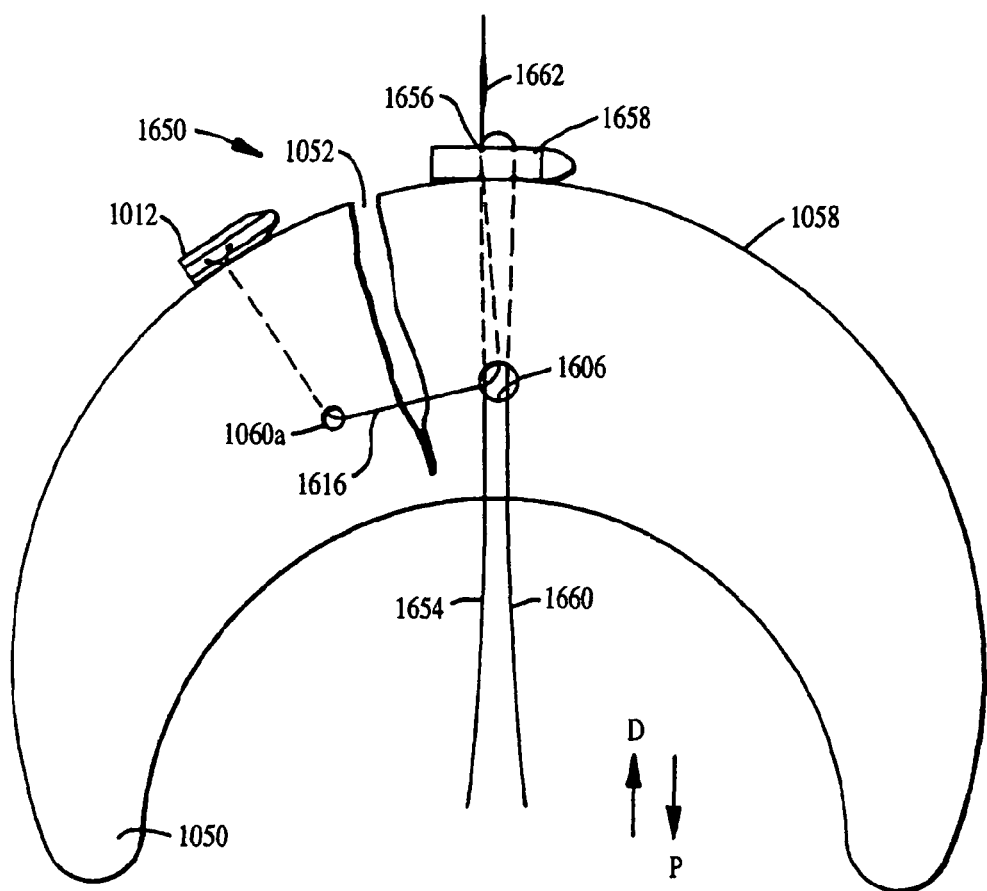
FIG. 32 is a perspective, partially schematic view of an alternative wound closure device implanted within a meniscus.

The second anchor can employ one-way tightening schemes other than a "one-way knot." For example, referring to FIG. 32, a device 1650 includes first anchor 1012, a second anchor 1615, and two sutures 1616 and 1654. Second anchor 1615 has a generally cylindrical shape, and defines two through-holes 1656 and 1658. When anchors 1012 and 1615 are positioned against backside 1058 of meniscus 1050, suture 1616 passes from first anchor 1012, through holes 1060*a* and 1060*b* in the meniscus, and then through holes 1656 and 1658 of anchor 1615, terminating at free end 1660. Suture 1616 does not form a one-way knot at second anchor 1615. Instead, suture 1616 simply passes through holes 1656 and 1658 in succession, such that anchor 1615 acts as a pulley anchor.

The second suture, suture 1654, passes only through hole 1656 of anchor 1615, and through hole 1060*b* of the meniscus. A portion 1662 of suture 1654, distal to hole 1656, is thicker than the remainder of suture 1654. This thicker portion 1662 cannot pass through hole 1656. (The thickness of portion 1662 is exaggerated in FIG. 32.)

In operation, a surgeon deploys the two anchors as described above with respect to other embodiments, and then pulls on free end 1660 of suture 1616 to position the anchors against backside 1058 and close the tear in the meniscus. Once suture 1616 is tensioned to the surgeon's satisfaction, the surgeon pulls on suture 1654 in the proximal direction (arrow P), until a segment of portion 1662 wedges into hole 1656. Portion 1662 wedges suture 1616 in place within hole 1656, preventing the length of suture 1616 between the two anchors from increasing, and thereby locking the two anchors in place.

Modifications of other portions of wound closure device 1010 are also possible. For example, the fin-shaped projection 1020 of the first anchor need not have the shape shown in the figures. Other types of projections capable of protruding through a needle opening and engaging tissue can be used. In addition, as described above with reference to FIG. 21A, the first anchor need not include any projection, but can instead be a simple cylinder defining holes for affixation of the suture.

Instead of attaching the suture to the first anchor using a conventional knot 1025, the suture can be welded or glued to the anchor, or can be spliced.

Figure 33A:
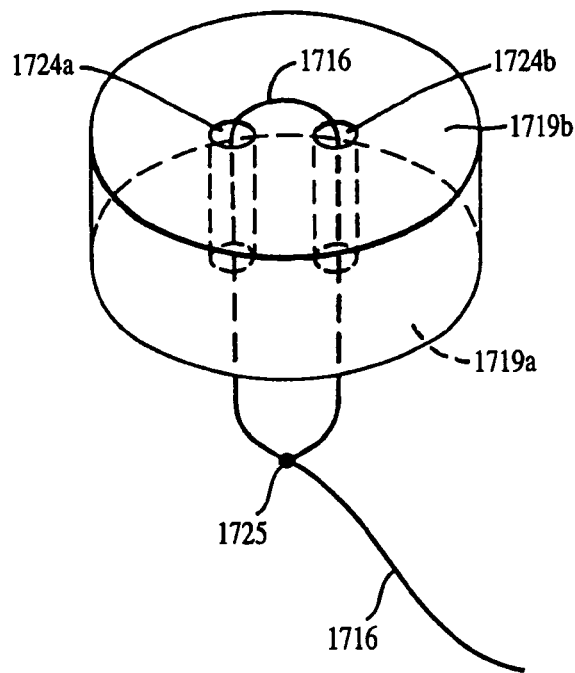
FIG. 33A is a perspective view of an alternative first suture anchor design for a wound closure device.

Referring to FIG. 33A, the first anchor need not include an extended, cylindrical body, but can instead have a button-shaped body. Button-shaped first anchor 1712 includes a circular distal side 1719*a* and a circular proximal side 1719*b*. Two axial holes 1724*a* and 1724*b* pass from side 1719*a* to side 1719*b*. A suture 1716 is attached to anchor 1712 by passing through hole 1724*a* in a first direction, through hole 1724*b* in a second direction, and then forming a conventional knot 1725 on the distal side of the anchor.

Figure 33B:
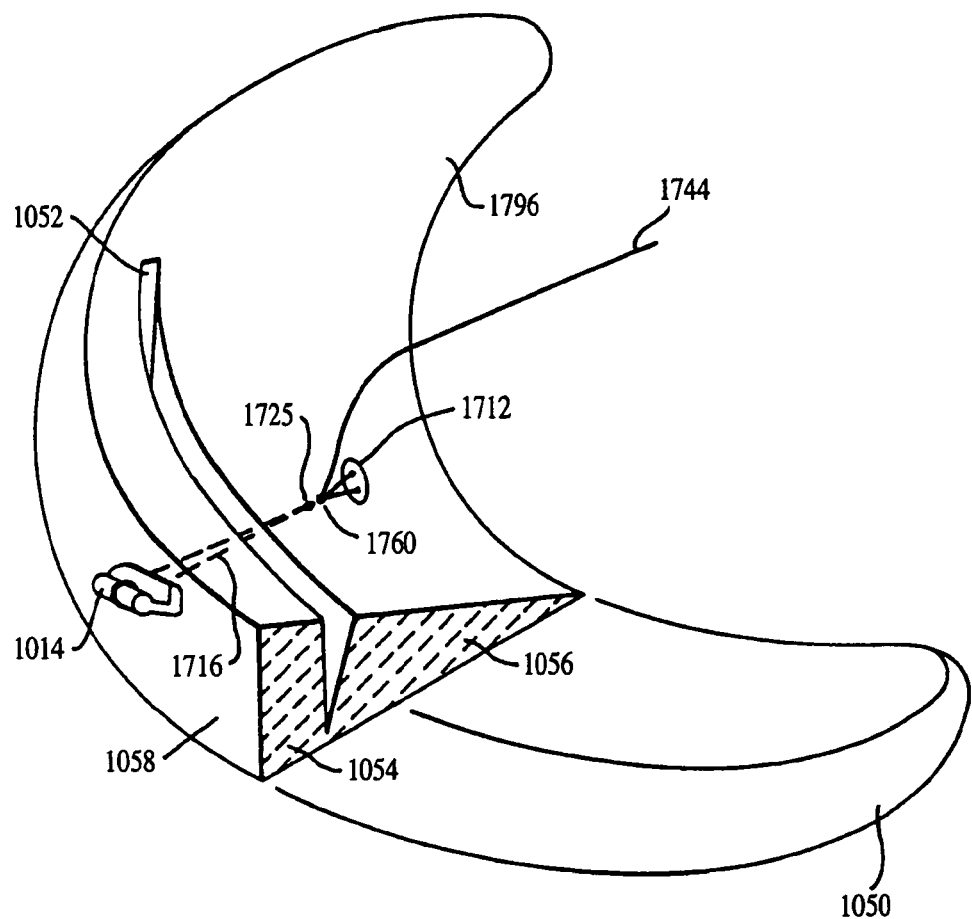
FIG. 33B is a perspective, cut-away view of the wound closure device of FIG. 33A implanted within a meniscus.

Referring to FIG. 33B, button-shaped first anchor 1712 is deployed against a proximal surface 1796 of meniscus 1050, and second anchor 1014 is deployed against surface 1058. Suture 1716 passes from first anchor 1712 into proximal tissue 1056 at point 1760, such that knot 1725 is located within the tissue. From point 1760, suture 1716 passes across tear 1015 to second anchor 1014, then through second anchor 1014 in the manner described above with reference to FIG. 16. From second anchor 1014, the suture passes back into distal tissue 1054, across tear 1015, and emerges from proximal tissue 1056 at point 1760. The suture then terminates at free end 1744. As with the embodiments described above, pulling on free end 1744 tensions the suture and closes the tear.

Alternatively, button-shaped anchor 1712 can be deployed on the distal side of the tear adjacent second anchor 1014, using the methods described above with reference to FIGS. 17, 20A-20D, 21A-21D, and 22A-22D.

The second anchor need not include a groove 1035 to allow passage of a plunger. Instead, the second anchor can define an axial through-hole for passage of the plunger.

Rather than a suture, the first and second anchors can be connected with other types of flexible members.

The wound closure device can include more than two suture anchors. For example, in addition to the first and second anchors, the device can include a third anchor identical in structure and function to the second anchor. In operation, after deploying the second anchor against surface 1058 of meniscus 1050, the surgeon could again pass the suture across tear 1015, adding an additional stitch, and then deploy the third anchor against surface 1058. After deploying all three anchors, the surgeon would pull on the free end of the suture, causing the suture to slide over both the second and third anchors, shortening the length of suture between the third and first anchors, and thereby closing the wound.

When more than two anchors are used, one or more of the anchors can be a pulley, such as pulley anchor 1813 described above with reference to FIG. 29. For example, the device could include a first anchor 1012, a pulley anchor 1813, and a second anchor 1014. The suture would be affixed to the first anchor, would slide over the pulley anchor, and form a one-way knot at the second anchor.

Depending on the size of the tissue wound, more than three anchors can be used. The additional anchors can all be pulley anchors, can all be similar to the second anchor, or can be both additional pulleys and additional second anchors.

The wound closure devices need not be deployed using a needle, and need not be deployed arthroscopically. Instead, a surgeon can place the anchors against the tissue during an open procedure.

The wound closure devices can be used to repair tissue wounds other than meniscal tears. For example, the devices can be used to repair tears in skin, muscles, and ligaments, and to re-attach tissue to support structures, such as bones.

Figure 34:
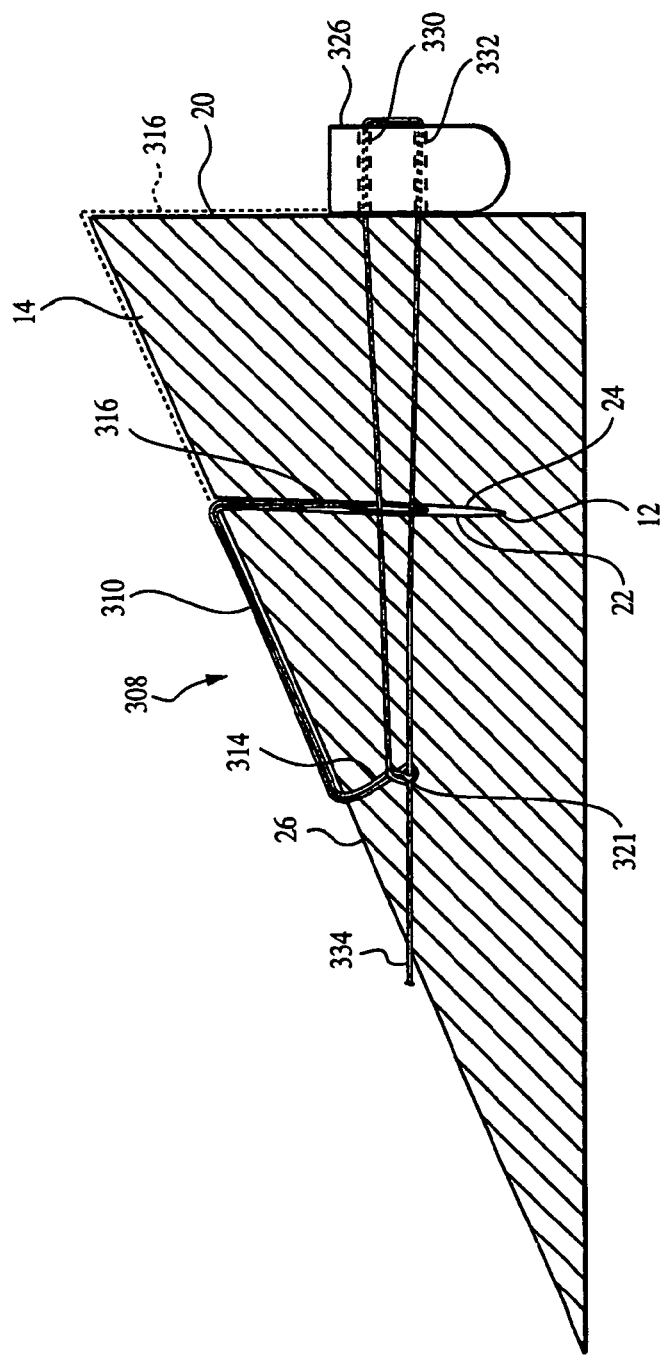
FIG. 34 is a cross-sectional side view of an alternative embodiment of a closure device, shown mending a tear in soft tissue.

Referring to FIGS. 34-36, a device 308 for repairing a tear 12 in tissue 14 includes a suture 310 attached to a single fixation member 326. Fixation member 326 defines through holes 330, 332 for receiving suture 310. Suture 310 has a first end 312 attached to suture 310 at point 314 (as described above with reference to FIG. 2B) to form a looped end 316 remote from fixation member 326, and a second, free end 334.

When implanted in the knee joint, fixation member 326 lies on a surface 20 of tissue 14. Looped end 316 is located in tear 12 and extends along surface 26 of tissue 14. Suture 310 extends through tissue 14, passing through looped end 316 in tear 12, and emerging at tissue surface 20 where suture 310 loops through fixation member 326. Suture 310 extends back through tissue 14, passing through looped end 316 in tear 12 and through a slip knot 321 formed in suture 310, and emerging at tissue surface 26. As described further below, after device 308 is positioned in tissue 14, the user pulls on free end 334 of suture 310, in the direction of arrow 150, to bring sides 22, 24 of tear 12 together into juxtaposition (as shown in FIG. 34). Slip knot 321 limits loosening of suture 310. Alternatively, looped end 316 is located on surface 20 between fixation member 326 and surface 20, as shown in dashed line in FIG. 34.

Figure 37:
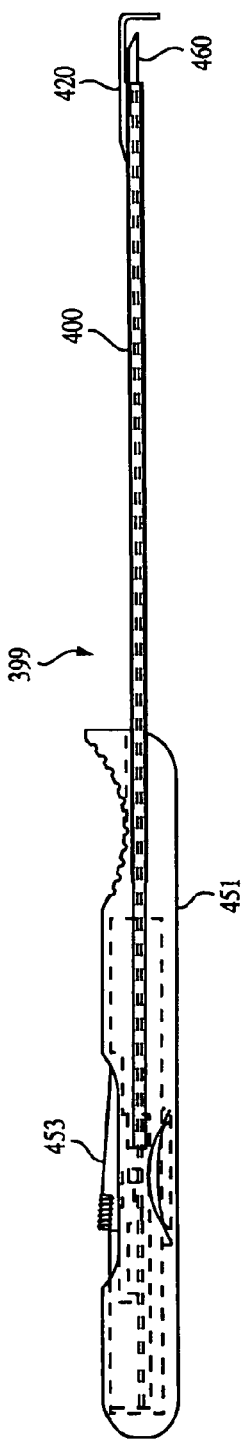
FIG. 37 is a side view of a delivery device for inserting the closure device of FIG. 34 in soft tissue.
Figure 37A:
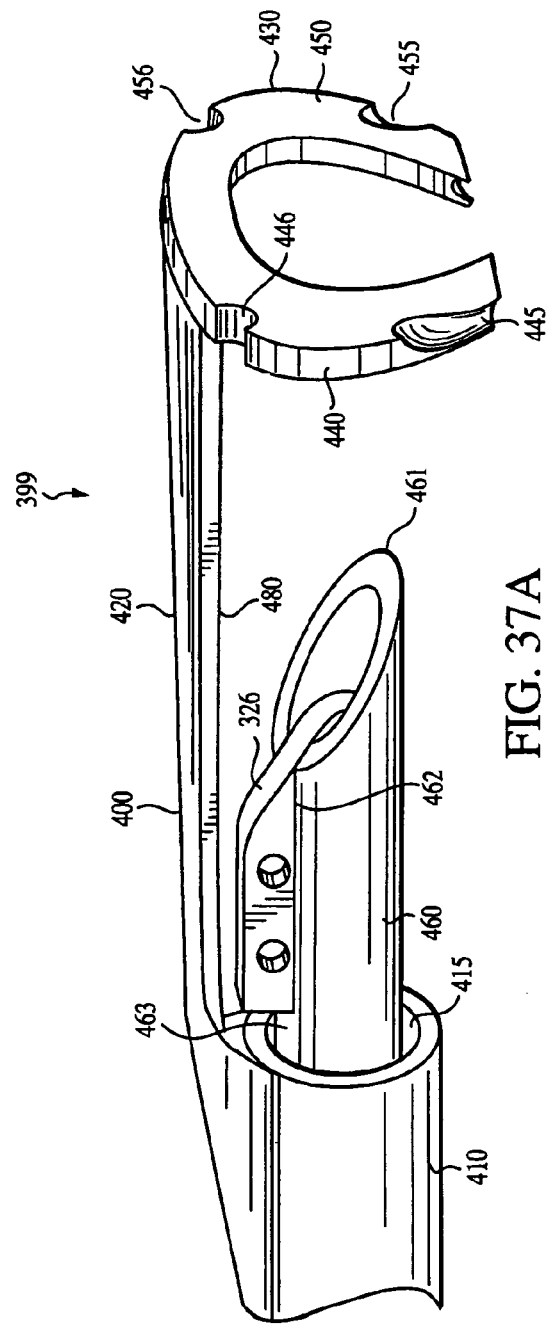
FIG. 37A is a perspective view of a distal section of the delivery device of FIG. 37 shown with a fixation member of the closure device of FIG. 34.

Referring to FIGS. 37-37B, a delivery device 399 for implanting device 308 includes a suture holder 400 and needle 460. Suture holder 400 includes a tube 410 defining a lumen 415 through which needle 460 extends, a shaft 420, and a distal portion 430. Distal portion 430 has a first tine 440 defining grooves 445 and 446, and a second tine 450 defining grooves 455, 456. Needle 460 has a beveled tip 461 and a slot 462 in a top portion 463 of needle 460.

When assembled, fastening member 326 with attached suture 310 is positioned in slot 462 with suture 310 preformed with looped end 316 and slip knot 321. Slip knot 321 is formed as described above with reference to FIGS. 2A-2I, though where fixation member 16 is positioned in FIGS. 2A-2I, suture 310 is formed as looped end 316 (FIG. 37C). Looped end 316 is positioned on suture holder 400 within grooves 445, 446, 455 and 456 of tines 440, 450 (FIG. 37B), and extends along a bottom side 480 of shaft 420. As shown in FIG. 37, delivery device 399 includes a handle 451 with a push knob 453 for advancing needle 460 relative to suture holder 400.

Figure 38:
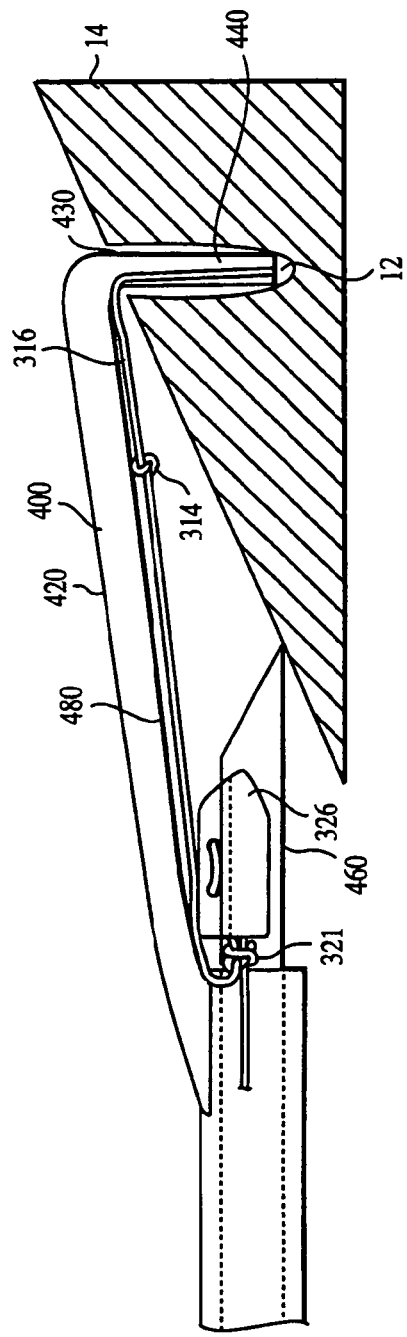
FIGS. 38-40 show the delivery device of FIG. 37 in use inserting the closure device of FIG. 34 in soft tissue.
Figure 39:
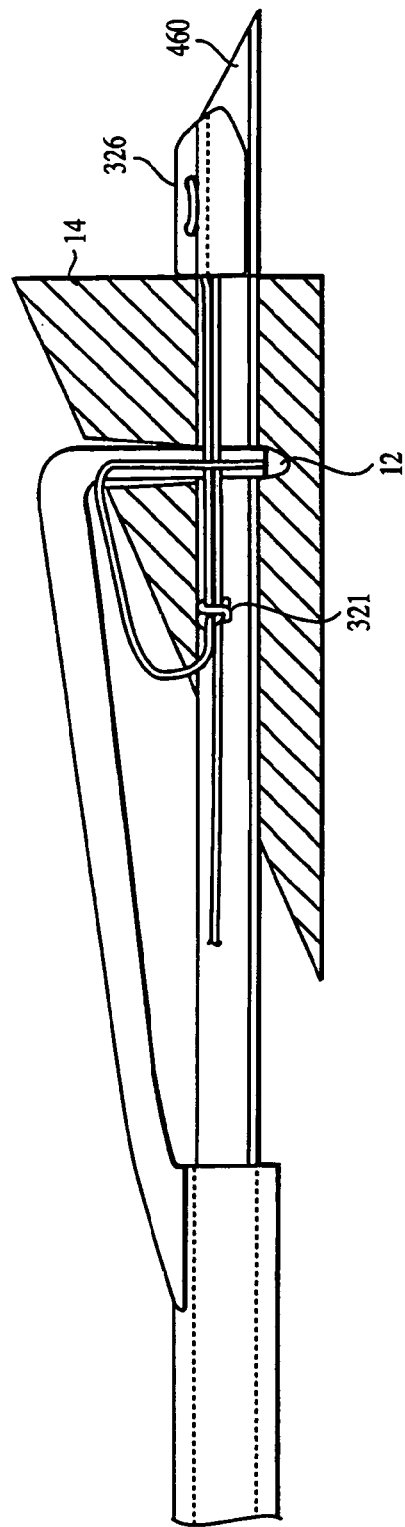
Figure 40:
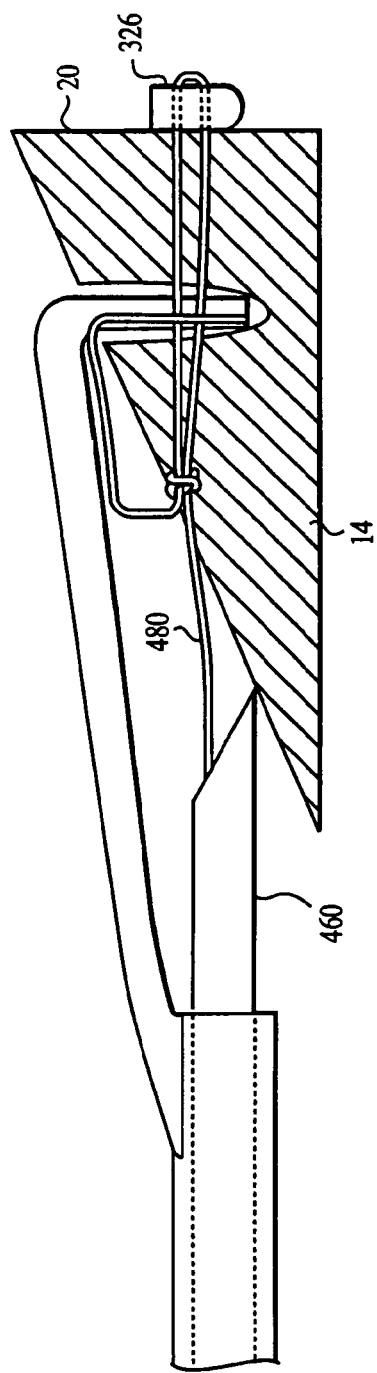

Referring to FIG. 38, in use, the user inserts distal portion 430 of suture holder 400 into tear 12 of tissue 14, and then advances needle 460 through tissue 14, traversing tear 12, and exiting tissue 14 at tissue surface 20. Needle 460 passes between tines 440 and 450, and thus through looped end 316 of suture 310 (FIG. 39). The user then retracts needle 460 from tissue 14 (FIG. 40). The contact of fastening member 326 with tissue surface 20 during the retraction of needle 460 acts to push fastening member 326 out of needle 460 such that fastening member 326 remains at surface 20, as described above with reference to FIG. 7. Pulling on free end 334 of suture 310 brings sides 22, 24 of tear 12 into juxtaposition. Slip knot 321 secures device 308 in place. Excess suture 310 can then be cut off.

Figure 41:
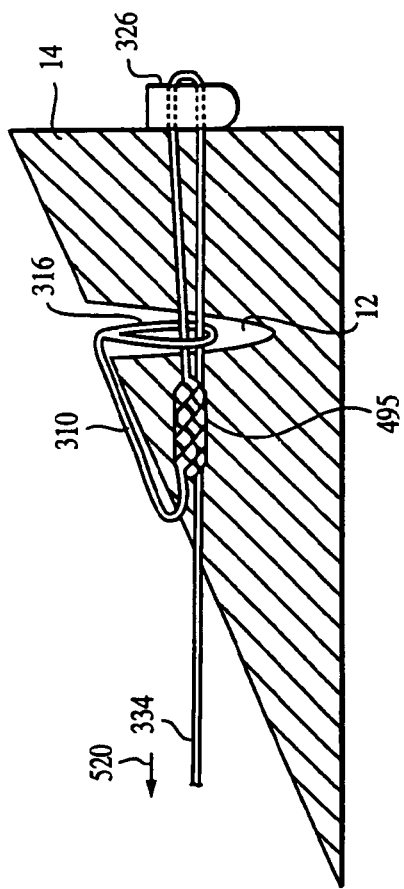
FIG. 41 is a cross-sectional side view of the closure device of FIG. 34 with an alternative embodiment of a retaining element, shown mending a tear in soft tissue.

Referring to FIG. 41, rather than securing device 308 with a slip knot, suture 310 includes a retaining element in the form of a Chinese trap or hand cuff 495, that is, an element that when pulled on, tightens around something disposed within the element. Free end 334 of suture 310 is slidably received within trap 495. When free end 334 of suture 310 is pulled in the direction of arrow 150 trap 495 is stretched, eventually gripping suture passing therethrough to secure suture 310 and device 308. The retaining element can also take the form of retaining elements described above with reference to FIGS. 12-12C and 13.

Figure 42:
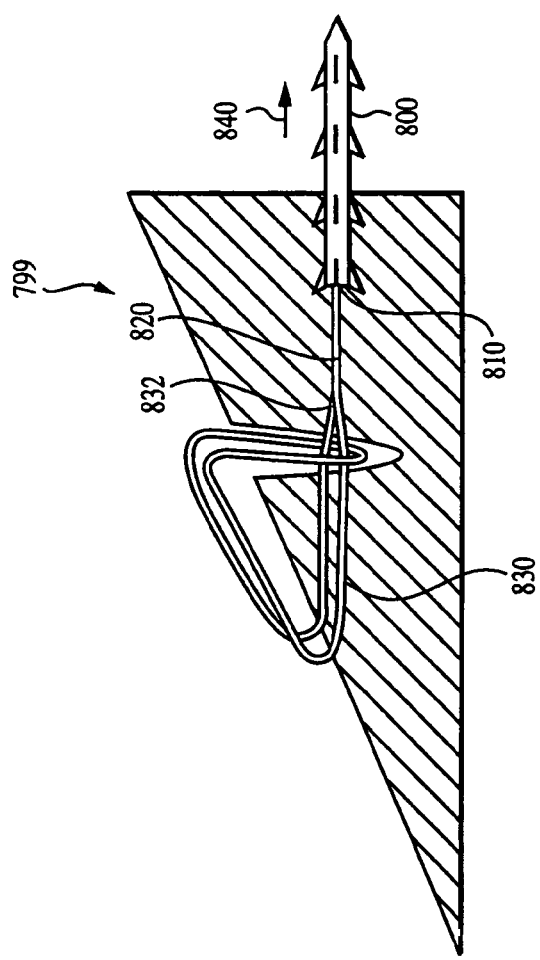
FIG. 42 is a cross-sectional side view of an alternative embodiment of a closure device, similar in use to the closure device of FIG. 34.

Referring to FIG. 42, a device 799 for repairing tear 12 in tissue 14 includes a barbed fastening member 800 and a suture 820. Suture 820 has an end 810 attached to fastening member 800. Suture 820 is formed in loop 830 with a second end 832 of suture 820 attached to suture 820. Delivery device 399 can be used to deploy device 799 with suture 820 being tightened to close tear 12 by pushing fastening member 800 in the direction of arrow 840, rather than pulling on a free end of suture. Barbed fastening member 800 limits loosening of suture 820.

Figure 43:
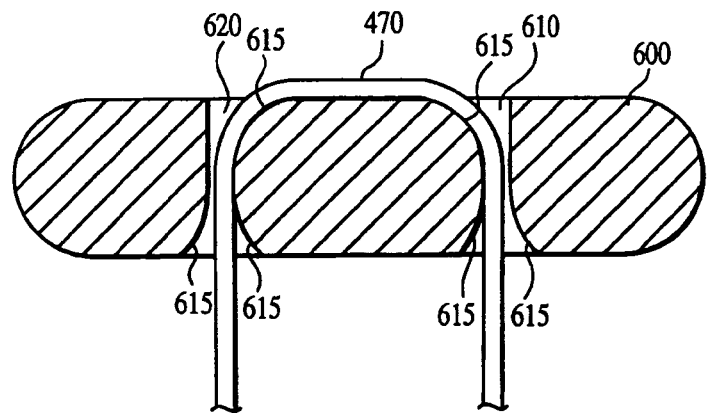
FIGS. 43 and 44 are alternative embodiments of a fixation member of the closure device of FIG. 34.
Figure 44:
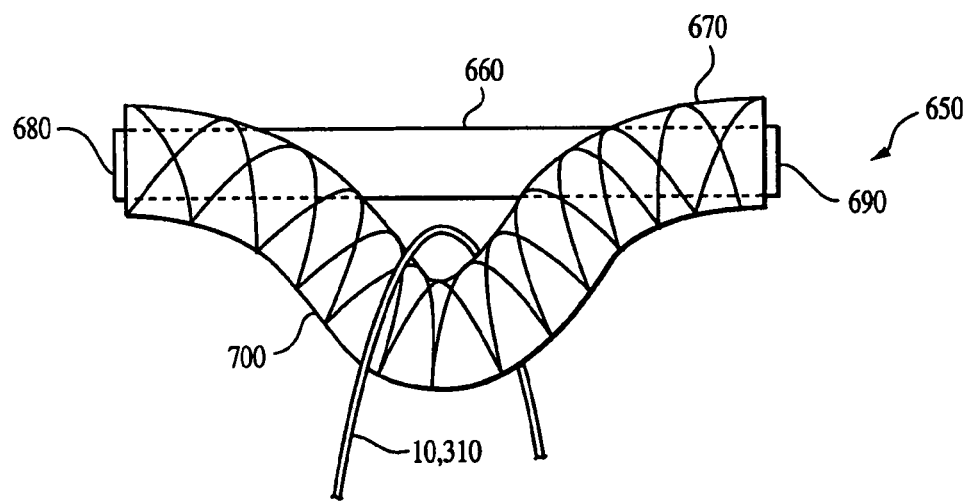

Referring to FIG. 43, an alternative embodiment of a fixation member 600 includes through bores 610, 620 with radiused corners 615 to reduce friction between suture 470 and fixation member 600. Referring to FIG. 44, another embodiment of a fixation member 650, which can be used in any of the above embodiments, includes a solid rod 660 with ends 680, 690, and a braided suture 670 attached to ends 680, 690. Suture 670 forms a loop 700 for receiving suture 10 or suture 310. Loop 700 lines up with suture 10, 310 to act as a pulley and reducing friction between the suture and fixation member.

The fixation members, securement elements, and suture of the above embodiments can be formed of a biodegradable material.

Other embodiments are within the scope of the following claims.

What is claimed is:
1. A wound closure device comprising:
a first anchor;
a second anchor; and
a flexible member connecting the first anchor to the second anchor, the flexible member including a first end which is coupled relative to the first anchor and a free end which is looped through the second anchor and through a slip fastener, whereby the flexible member is movably attached to the second anchor, such that pulling on the free end of the flexible member shortens a length of the flexible member between the first anchor and second anchor,
wherein the movable attachment includes a knot formed in the flexible member at the second anchor, wherein the knot includes a first portion of the flexible member threaded through the second anchor to form a loop, and a second portion that passes over a surface of the second anchor and through the loop.

2. The wound closure device of claim 1, wherein the movable attachment of the flexible member to the second anchor enables the length of the flexible member between the first and second anchors to be shortened, but not lengthened.

3. The wound closure device of claim 1, wherein the surface comprises an exterior surface of the second anchor.

4. The wound closure device of claim 1, wherein the knot is configured such that pulling on the free end causes the flexible member to slide through the loop to shorten the length of the flexible member between the first and second anchors, but pulling on the flexible member in an opposite direction in order to increase the length of the flexible member between the first and second anchors causes the loop to press the second portion against a compression surface of the second anchor, resisting increase in the length of flexible member between the first and second anchors.

5. The wound closure device of claim 1, wherein the second portion includes the free end.

6. The wound closure device of claim 1, wherein the second anchor defines a partially enclosed region, and the loop is formed within the partially enclosed region.

7. The wound closure device of claim 6, wherein the second anchor includes a second section that defines a passage that connected to the partially enclosed region, and the free end of the suture passes through the passage.

8. The wound closure device of claim 1, wherein the second anchor includes a first section that defines a plurality of holes, and wherein the knot is formed by a first portion of the flexible member passing through a plurality of holes to form a loop and a second portion of the flexible member passing over a surface of the second anchor and through the loop.

9. A wound closure device comprising:
a first anchor;
a second anchor;
a flexible member connecting the first anchor to the second anchor, the flexible member being movably attached to the second anchor, such that pulling on a free end of the flexible member shortens a length of the flexible member between the first anchor and second anchor; and
a slip fastener;
wherein the free end is a first end of the flexible member, the flexible member further including a second end, the second end coupled to the first anchor; and
wherein the second anchor includes a loop through which the flexible member passes, the flexible member slidably passing through the slip fastener and the loop.

10. The wound closure device of claim 9, wherein the first anchor and the second anchor are configured to anchor into bone;
wherein the flexible member between the first anchor and the second anchor passes through tissue; and
wherein pulling on the free end of the flexible member reduces the length of the flexible member between the first anchor and the slip fastener, bringing the tissue end into secure contact with the bone.

11. The wound closure device of claim 9, wherein the flexible member between the first anchor in the second anchor passes multiple times through a tear in tissue; and
wherein pulling on the free end of the flexible member reduces the length of the flexible member between the first anchor and the slip fastener, closing the tear.

12. A wound closure device comprising:
a first anchor;
a second anchor; and
a flexible member connecting the first anchor to the second anchor, the flexible member including a first end which is coupled relative to the first anchor and a free end which is looped through the second anchor and through a slip fastener, whereby the flexible member is movably attached to the second anchor, such that pulling on the free end of the flexible member shortens a length of the flexible member between the first anchor and second anchor,
wherein the device is configured such that tensioning a portion of the flexible member extending between the first anchor and the second anchor while not tensioning the free end causes the second anchor to pin the flexible member between the second anchor and a compression surface thereby resisting relative movement between the second anchor and the flexible member and thus resisting an increase in length of the flexible member between the first and second anchors.

13. The wound closure device of claim 12, wherein the second anchor includes a first section that defines a plurality of holes, and wherein the movable attachment includes a knot formed by a first portion of the flexible member passing through a plurality of holes to form a loop and a second portion of the flexible member passing over a surface of the second anchor and through the loop.

14. The wound closure device of claim 12, wherein the second anchor includes a first section that defines a plurality of holes, wherein the free end is looped through the first hole and back through the second hole.

15. The wound closure device of claim 12 wherein the slip fastener slidably secures the free end of the flexible member relative to the second anchor.

16. The wound closure device of claim 12, wherein the slip fastener slidably secures the free end of the flexible member relative to first portion of the flexible member extending between the first anchor and the second anchor.

* * * * *